US011266350B2

(12) United States Patent
Saroka et al.

(10) Patent No.: US 11,266,350 B2
(45) Date of Patent: Mar. 8, 2022

(54) ADHESIVE PATCHES FOR THE ATTACHMENT OF RADIOFREQUENCY (RF) ELECTROMAGNETIC (EM) CUP-SHAPED PROBE WITH RADIATION ABSORBING MATERIAL

(71) Applicant: Sensible Medical Innovations Ltd., Kfar Neter (IL)

(72) Inventors: Amir Saroka, Tel-Aviv (IL); Shlomi Bergida, Udim (IL)

(73) Assignee: Sensible Medical Innovations Ltd., Netanya (IL)

( * ) Notice: Subject to any disclaimer, the term of this patent is extended or adjusted under 35 U.S.C. 154(b) by 1147 days.

(21) Appl. No.: 14/398,525

(22) PCT Filed: May 2, 2013

(86) PCT No.: PCT/IL2013/050373
§ 371 (c)(1),
(2) Date: Nov. 3, 2014

(87) PCT Pub. No.: WO2013/164827
PCT Pub. Date: Nov. 7, 2013

(65) Prior Publication Data
US 2015/0133763 A1    May 14, 2015

Related U.S. Application Data

(60) Provisional application No. 61/641,919, filed on May 3, 2012.

(51) Int. Cl.
*A61B 5/00* (2006.01)
*A61B 5/0507* (2021.01)
(Continued)

(52) U.S. Cl.
CPC .............. *A61B 5/6833* (2013.01); *A61B 5/05* (2013.01); *A61B 5/0507* (2013.01); *A61B 5/24* (2021.01)

(58) Field of Classification Search
CPC ........... A61B 5/6833; A61B 5/05; A61B 5/04; A61B 5/0507; A61B 5/24
See application file for complete search history.

(56) References Cited

U.S. PATENT DOCUMENTS

| 5,879,373 A | 3/1999 | Roeper et al. |
| 6,233,479 B1 | 5/2001 | Haddad et al. |

(Continued)

FOREIGN PATENT DOCUMENTS

| EP | 2800510 | 11/2014 |
| WO | WO 2009/031149 | 3/2009 |

(Continued)

OTHER PUBLICATIONS

Communication Pursuant to Article 94(3) EPC Dated Jan. 24, 2017 From the European Patent Office Re. Application No. 13733053.6. (6 Pages).

(Continued)

*Primary Examiner* — Serkan Akar

(57) ABSTRACT

An adhesive patch for attaching at least one EM probe to a subject's body, the adhesive patch comprising a planar member having at least one layer of radiation absorbing material and having at least one opening formed within the radiation absorbing material to allow the propagation of EM radiation via the opening from one side of the planar member to the other. The adhesive patch further comprises at least one layer of an adhesive attached over at least part of a bottom surface of the planar member, which adhesive layer may be applied so as to form a pattern on the bottom (Continued)

surface, the pattern comprising at least one adhesive-covered portion and at least one adhesive-free portion.

14 Claims, 27 Drawing Sheets

(51) Int. Cl.
*A61B 5/24* (2021.01)
*A61B 5/05* (2021.01)

(56) References Cited

U.S. PATENT DOCUMENTS

| | | | |
|---|---|---|---|
| 7,184,824 B2 | 2/2007 | Hashimshony | |
| 7,591,792 B2 | 9/2009 | Bouton | |
| 2003/0036674 A1 | 2/2003 | Bouton | |
| 2003/0113827 A1 | 6/2003 | Burkoth | |
| 2006/0224056 A1 | 10/2006 | Kermani et al. | |
| 2007/0228071 A1 | 10/2007 | Kamen et al. | |
| 2010/0249558 A1* | 9/2010 | Yodfat | A61M 5/14248 600/345 |
| 2010/0324403 A1* | 12/2010 | Brister | A61B 5/1411 600/365 |
| 2011/0160549 A1 | 6/2011 | Saroka et al. | |
| 2013/0060115 A1* | 3/2013 | German | A61B 5/0416 600/372 |
| 2013/0079611 A1* | 3/2013 | Besko | A61B 5/14552 600/344 |

FOREIGN PATENT DOCUMENTS

| | | |
|---|---|---|
| WO | WO 2009/031150 | 3/2009 |
| WO | WO 2010/100649 | 9/2010 |
| WO | WO 2011/076871 | 6/2011 |
| WO | WO 2011/141915 | 11/2011 |
| WO | WO 2013/105086 | 7/2013 |
| WO | WO 2013/164827 | 11/2013 |

OTHER PUBLICATIONS

Office Action dated Apr. 24, 2018 From the Israel Patent Office Re. Application No. 235479 and Its Translation Into English. (6 Pages).
Communication Relating to the Results of the Partial International Search dated Aug. 22, 2013 From the International Searching Authority Re. Application No. PCT/IL2013/050373.
International Preliminary Report on Patentability dated Nov. 13, 2014 From the International Bureau of WIPO Re. Application No. PCT/IL2013/050373.
International Search Report and the Written Opinion dated Oct. 28, 2013 From the International Searching Authority Re. Application No. PCT/IL2013/050373.
Communication Pursuant to Article 94(3) EPC Dated Dec. 11, 2018 From the European Patent Office Re. Application No. 13733053.6. (7 Pages).
Office Action dated Jul. 17, 2019 From the Israel Patent Office Re. Application No. 235479 and Its Translation Into English. (8 Pages).

* cited by examiner

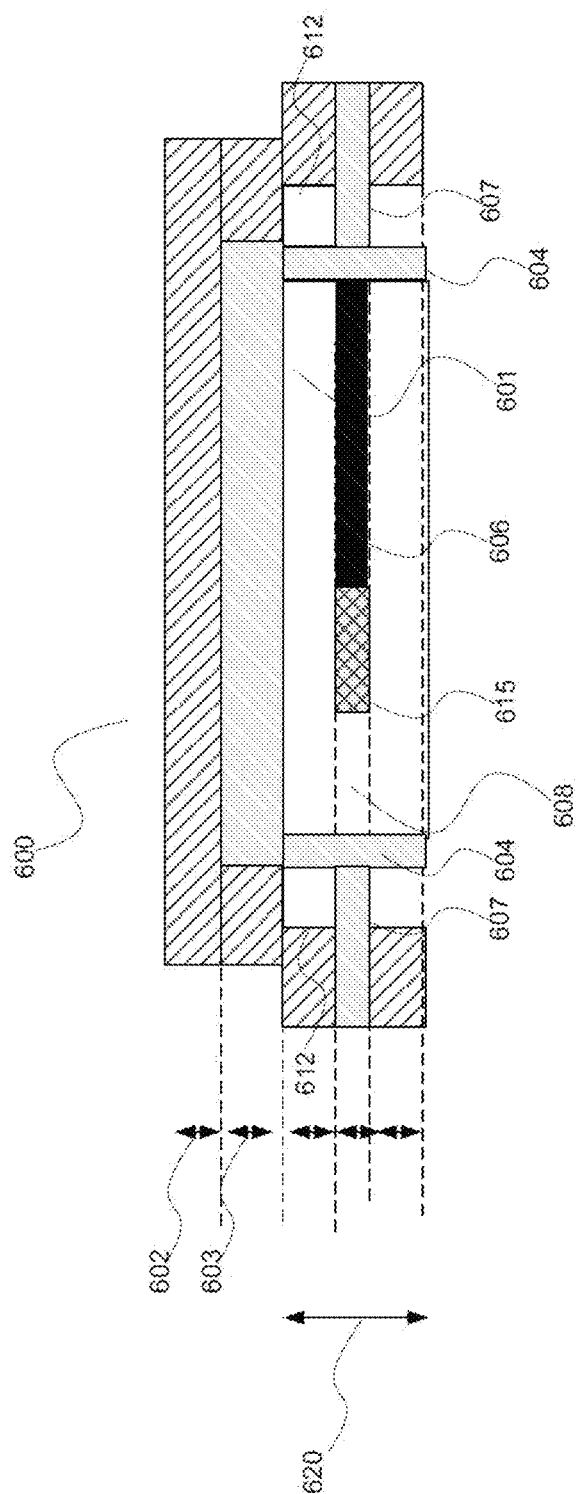
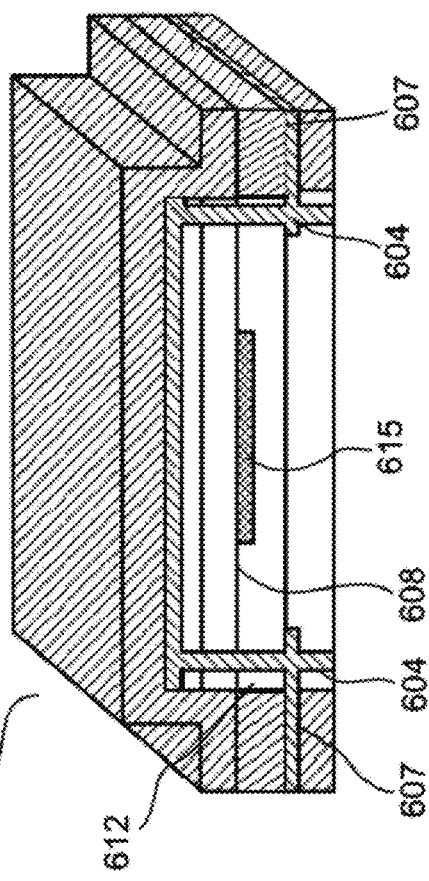
FIG. 10A
FIG. 10B

ADHESIVE PATCHES FOR THE ATTACHMENT OF RADIOFREQUENCY (RF) ELECTROMAGNETIC (EM) CUP-SHAPED PROBE WITH RADIATION ABSORBING MATERIAL

RELATED APPLICATIONS

This application is a National Phase of PCT Patent Application No. PCT/IL2013/050373 having International filing date of May 2, 2013, which claims the benefit of priority under 35 USC § 119(e) of U.S. Provisional Patent Application No. 61/641,919 filed on May 3, 2012. The contents of the above applications are all incorporated by reference as if fully set forth herein in their entirety.

FIELD AND BACKGROUND OF THE INVENTION

The present invention, in some embodiments thereof, relates to an electromagnetic EM probe and, more particularly, but not exclusively, to an EM probe for transmission and/or reception of electromagnetic radiation and a method of generating the EM probe.

EM radiation, such as RF and MW radiation, is potentially useful means of monitoring and diagnosing body tissues. The dielectric properties of the tissues may be a basis of detecting various pathologies and physiological trends.

Examples for using RF and MW radiation for monitoring and diagnosing body tissues is found, inter alia, in International patent application pub. No WO 2010/100649, International patent application pub. No WO 2009/031150, and/or International patent application pub. No 2009/031149, which are incorporated herein by reference. The design and fabrication of such EM probes present various challenges.

During the last years, various EM probes have been developed. For example U.S. Pat. No. 6,233,479 describes a Microwave Hematoma Detector which is a non-invasive device designed to detect and localize blood pooling and clots near the outer surface of the body. While being geared towards finding subdural and epidural hematomas, the device can be used to detect blood pooling anywhere near the surface of the body. Modified versions of the device can also detect pneumothorax, organ hemorrhage, atherosclerotic plaque in the carotid arteries, evaluate perfusion (blood flow) at or near the body surface, body tissue damage at or near the surface (especially for burn assessment) and be used in a number of NDE applications. The device is based on low power pulsed microwave technology combined with a specialized antenna, signal processing/recognition algorithms and a disposable cap worn by the patient which will facilitate accurate mapping of the brain and proper function of the instrument. The invention may be used for rapid, non-invasive detection of subdural or epidural hematoma in human or animal patients, detection of hemorrhage within approximately 5 cm of the outer surface anywhere on a patient's body.

Another example is described in U.S. Pat. No. 7,184,824 which describes an EM probe for examining tissue in order to differentiate it from other tissue according to the dielectric properties of the examined tissue are provided. The EM probe includes an inner conductor, having a plurality of sharp, thin, conductive spikes, at a proximal end with respect to a tissue for examination, the plurality of sharp, thin, conductive spikes being operative to enhance the electrical fringe fields, where interaction with the tissue for examination occurs.

Another example is described in U.S. Pat. No. 7,591,792 which describes: a tissue sensors house for one or more sensor elements. Each element has a housing mounted substrate and a superstrate with a planar antenna between. A transitional periphery (TP) of a superstrate outer surface interconnects a base to a plateau. At least some of the TP has a generally smooth transition. Plural elements are spaced by the housing. Alternately, the superstrate TP is flat, the housing extends to the outer superstrate surface and a shield surrounds the element. The housing is flush with or recessed below the superstrate and defines a TP between the housing and superstrate. A method converts a reference signal to complex form; plots it in a complex plane as a reference point (RP); converts a measurement signal to complex form; plots it in the complex plane as a measurement point (MP); determine a complex distance between the MP and the RP; and compares complex distance to a threshold.

SUMMARY OF THE INVENTION

According to some embodiments of the present invention there is provided an electromagnetic (EM) probe for monitoring at least one biological tissue. The EM probe comprises a cup shaped cavity having an opening and an interior volume, a circumferential flange formed substantially around the cup shaped cavity, in proximity to the opening, at least one layer of a material, for absorbing electromagnetic radiation, applied over at least one of a portion of the circumferential flange and a portion of the outer surface of the cup shaped cavity, and at least one EM radiation element which performs at least one of emitting and capturing EM radiation via the interior volume.

Optionally, the at least one layer covers at least the edge of the bottom surface of the circumferential flange.

Optionally, the portion of the at least one layer covers at least 25% of the bottom surface of the circumferential flange.

Optionally, at least part of the circumferential flange is set to be detachably connected to the cup shaped cavity.

More optionally, the circumferential flange is set to be affixed to a monitored user so as to allow detachably connecting the cup shaped cavity thereto, in a manner that the opening faces a skin area of the monitored user.

Optionally, the at least one EM radiation element is placed in the interior volume.

Optionally, the at least one EM radiation element is placed outside of the interior volume and connected by a waveguide to the cup shaped cavity.

Optionally, the circumferential flange and cup shaped cavity are molded as a single unit.

Optionally, the at least one layer is applied over at least one of a bottom side of the circumferential flange and a top side of the circumferential flange.

Optionally, the circumferential flange is non-continuous.

Optionally, the circumferential flange is at least partly flexible.

Optionally, the circumferential flange is at least partly rigid.

Optionally, the circumferential flange is zigzagged along a plane parallel to the opening.

Optionally, the EM probe further comprises a processing unit, electrically connected to the emitting element, which performs at least one of controlling a transmission parameter of the emitted EM radiation and monitoring a biological tissue according to the captured EM radiation.

Optionally, the distance between the peripheral outer edge and the peripheral inner edge of the circumferential flange is at least 0.3 centimeters.

Optionally, the cup shaped cavity having a structure shape selected from a group consisting of: a box, a cube, a dome, a cone, and a pyramid.

Optionally, the EM radiation is reflected from a biological medium being in touch with the edges of the opening.

Optionally, the EM radiation is emitted by another EM radiation source, via a biological medium being substantially in front of the opening.

Optionally, the EM radiation source is another EM probe as defined in claim 1.

Optionally, the interior volume is filled with a dielectric substance.

Optionally, the EM probe is fabricated by a printed circuit board (PCB) fabrication method.

Optionally, the EM radiation is selected from a group consisting of radiofrequency (RF) radiation and microwave (MW) radiation.

Optionally, the circumferential flange is a non-circular circumferential flange.

Optionally, the circumferential flange is at least partly inside the cup shaped cavity.

Optionally, the circumferential flange is configured to form an airtight interface with a skin area of a patient, the airtight interface set to attach the EM probe to a skin area of a patient by air pressure differences.

Optionally, the EM probe is an intrabody probe.

According to some embodiments of the present invention there is provided a method of producing an electromagnetic (EM) probe for monitoring at least one biological tissue. The method comprises providing a cup shaped cavity having an opening and an interior volume, forming a circumferential flange substantially around the cup shaped cavity, applying at least one layer of a material for absorbing electromagnetic radiation over at least one of a portion of the circumferential flange and a portion of the outer surface of the cup shaped cavity, placing an emitting element configured for at least one of emitting and capturing EM radiation, and electrically connecting the emitting element to at least one of an EM receiver and an EM transmitter.

According to some embodiments of the present invention there is provided a method of monitoring at least one biological tissue. The method comprises providing a probe having a cup shaped cavity having an opening and an interior volume, a circumferential flange formed substantially around the cup shaped cavity, in proximity to the opening, at least one layer of a material, for absorbing electromagnetic radiation, applied over at least one of a portion of the circumferential flange and a portion of the outer surface of the cup shaped cavity, and at least one EM radiation element which performs at least one of emitting and capturing EM radiation via the interior volume and attaching the probe to a monitored user in a manner that the opening faces a skin area of the monitored user.

According to some embodiments, an adhesive patch is provided for attaching at least one EM probe to a subject's body, the adhesive patch comprising:
  a planar member comprising at least one layer of radiation absorbing material;
  at least one layer of an adhesive attached over at least part of a bottom surface of the planar member; and
  at least one opening formed within the at least one layer of radiation absorbing material to allow the propagation of EM radiation via the opening from one side of the planar member to the other.

In some embodiments, the radiation absorbing material is selected from the group of materials having at least one of the following:
  a permeability loss tangent of (tan $\delta=\mu''/\mu'$)>0.01 for all EM radiation frequencies within the range of 100 MHz-5 GHz;
  a permittivity loss tangent of (tan $\delta=\varepsilon''/\varepsilon'$)>0.01 for all EM radiation frequencies within the range of 100 MHz-5 GHz;
  a partial conduciveness manifested by a surface resistivity between 20 and 10,000 Ohm per square ($\Omega$/sq); and
  a volumetric resistivity greater than 10-3 Ohm meter ($\Omega$m).

Optionally the adhesive patch further comprises at least one mechanical connector for connecting (optionally in a detachable manner) the at least one EM probe to the planar member at a position overlapping the opening. Optionally, the adhesive patch includes a cover positioned over the opening, the cover being shaped and sized to receive an EM element.

Optionally, the adhesive patch comprises a battery for providing power to an EM probe when the EM probe is attached to the adhesive patch.

Optionally, the adhesive layer is attached over at least part of a surface covering 70% or less (or even 50% or less) of the patch contact surface, including or excluding surface area that is under an opening in the layer of radiation absorbing material. Optionally, the adhesive is attached over at least part of a surface of the planar member covering 50% or less.

Optionally, the adhesive is attached to the bottom surface of the adhesive patch at a pattern comprising at least one adhesive-covered portion and at least one adhesive-free portion, wherein the pattern is such that the adhesive patch may be attached to a surface area at at least a first position and at a second position such that:
  the portion of the surface area that is covered by the at least one opening of the adhesive patch at the first position overlaps the portion of the surface area covered by the opening of the adhesive patch at the second position by at least 30% or even by at least 90%; and
  the portion of the surface area that is covered by the at least one adhesive-covered portion of the adhesive patch at the first position overlaps the portion of the surface area that is covered by the at least one adhesive-covered portion of the adhesive patch at the second position by less than 30%, or by less than 10% or even not at all.

In some embodiments, the adhesive patch at the first position is at a first rotational orientation and the patch at the first position is at a second rotational orientation being different from the first rotational orientation, for example by 180° or by about 90°.

According to some embodiments of the invention, a set of adhesive patches is provided, the set comprising:
  a first adhesive patch having an adhesive attached over at least part of its surface at a first pattern, the first pattern comprising at least one adhesive-covered portion and at least one adhesive-free portion; and
  a second adhesive patch having an adhesive attached over at least part of its surface at a second pattern, the second pattern comprising at least one adhesive-covered portion and at least one adhesive-free portion;
  wherein the first pattern and the second pattern are such that the first adhesive patch and the second adhesive patch may be attached in sequence to a placement area with the portion of the placement area that is covered by the first adhesive patch overlapping the portion of the placement area that is covered by the second adhesive patch by at least 50% or even by at least 90%, and the portion of the placement area that is covered by the at least one adhesive-covered portion of the first adhesive patch overlaps the portion of the placement area that is covered by the at least one adhesive-covered portion of the second adhesive patch by less than 30%, or not at all.

According to some embodiments, an adhesive patch is provided for attaching at least one EM probe to a subject's body, the adhesive patch comprising:
- a planar member having at least one layer of an adhesive attached over at least part of a bottom surface of the planar member;
- at least one mechanical connector for connecting the at least one EM probe to the adhesive patch; and
- a battery for providing power to an EM probe when the EM probe is attached to the adhesive patch.

Optionally, the at least one of the at least one mechanical connector is configured for detachably connecting the EM probe to the adhesive patch.

Optionally, the adhesive patch may be configured for attaching a plurality of EM probes. For example, the adhesive patch may comprise a plurality of mechanical connectors for connecting a plurality of EM probes thereto. Optionally, the adhesive patch may comprise a plurality of batteries for providing power to one or more EM probes when they are attached to the adhesive patch.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. The patent or application file contains at least one drawing executed in color.

In the drawings:

FIG. 10A and FIG. 10B which are a sectional schematic illustration and a three dimensional illustration of a printed circuit board (PCB) EM probe having a fabricated cup shaped cavity, according to some embodiments of the present invention;

In FIG. 14A the adhesive patch is shown with an EM probe attached thereto and in FIG. 14B the adhesive patch is shown without an EM probe.

In FIG. 17A the planar member comprises at least one layer of radiation absorbing material having an opening therein. In FIG. 17B the planar member comprises a battery.

In FIG. 18A the pattern is shown at a first orientation, in FIG. 18B the pattern is shown at a second orientation and in FIG. 18C the pattern at the first orientation is superimposed on the pattern at the second orientation.

DESCRIPTION OF EMBODIMENTS OF THE INVENTION

Figure 1:
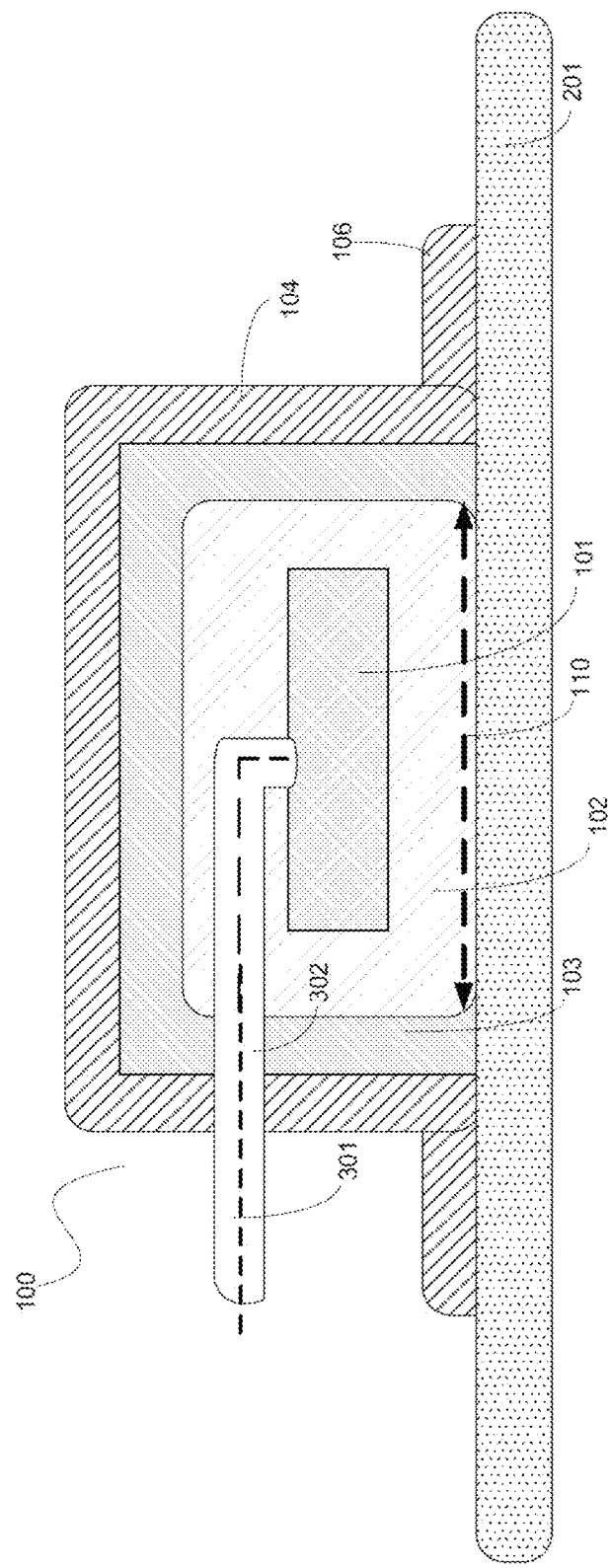
FIG. 1 is a schematic sectional illustration of an electromagnetic (EM) radiation EM probe for monitoring at least one biological tissue, according to some embodiments of the present invention.

The present invention, in some embodiments thereof, relates to an electromagnetic EM probe and, more particularly, but not exclusively, to an EM probe for transmission and/or reception of electromagnetic radiation and a method of generating the EM probe.

According to some embodiments of the present invention, there is provided an electromagnetic (EM) probe for monitoring dielectric properties in one or more biological tissues using a cup shaped cavity which is coated with one or more layers of absorbent material and has a circumferential flange. The cup shaped cavity houses an element for radiating and/or capturing EM radiation and has a single opening for the passage of the EM radiation. In such a manner, the cup shaped cavity forms a closed interference reduced volume when the opening is placed on top of or above a skin area of a monitored user. Such an EM probe is less sensitive to changes in the skin in an area outside the circumference of the EM probe, for example more than 2 cm, or more than 4 cm, and/or to changes which are introduced when the EM probe is being touched and/or changes which are related to the mechanical interfacing and/or coupling of the EM probe to the skin.

The circumferential flange is set to reduce the sensitivity to noise from the proximity of the EM probe, for example from external EM transmission sources, such as, for example, cellular phones, thus improving the signal to noise ratio (SNR) and therefore on the quality of reception. Moreover, the circumferential flange and the absorbing layers prevent from at least some of the EM transmissions to make their way to the external surface of the EM probe. In such a manner, the amount of escaped signals which add noise to the external environment may be reduced. It may reduce currents escaping or penetrating the EM probe to/from the external side of the EM probe or exposed body surfaces. Such currents may be conducted on the skin, or external conductive parts of the EM probe, like its cavity and/or conducting elements, such as cables. Such currents may, for example, be induced by currents related to a transmitting EM probe, or its connected cables, onto the conductive parts, or proximate skin area, of a receiving EM probe, via conduction or induction, resulting in parasitic crosstalk between them. The circumferential flange may be placed on the edge of the opening or attached to the external walls of the cup shape cavity few millimeters above the opening. The circumferential flange may be a bendable flange and/or a flexible flange which is adjusted to be closely attached to the skin surface of a monitored user. Optionally the flange is also set to assist in prevention of entry of fluid and/or water and/or perspiration into the area under the EM probe. Optionally, the flange is set to enable an airtight interface of the EM probe to the skin area, enabling attachment by air pressure differences of the EM probe, and/or increasing the effectiveness of the isolation functionality of the flange by improving the mechanical coupling of the flange to the skin area. For example by use of another layer, for example a sub millimeter layer of silicon material, covering the bottom side of the flange. The circumferential flange may be zigzagged, jagged, and/or curved to extend the path of signals passing therethrough. The absorbing material may cover external walls of the cup shaped cavity, the circumferential flange or any portion thereof, and/or a portion of the internal walls of the cup shaped cavity. A layer of absorbing material may be placed on the lower side of the circumferential flange so as to be in contact with the monitored skin area.

According to some embodiments of the present invention, the EM probe is a printed circuit board (PCB) EM probe fabricated in known fabrication techniques.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic sectional illustration of an electromagnetic (EM) radiation EM probe 100 for monitoring at least one biological tissue, according to some embodiments of the present invention. The EM probe 100 includes a cup shaped cavity 103 having an opening 110 and an interior volume 102. As FIG. 1 depicts a section illustration, the depicted broken line represents the diameter of the opening 110. The outer surface of the cup shaped cavity 103, namely the external sides of the cup shaped cavity 103 which do not face the interior volume 102 are covered with one or more layers 104 of a material for absorbing EM radiation. The one or more layers 104 are set to absorb electric fields and/or magnetic fields.

For example regarding the complex permittivity of the absorbing material at a frequency of about 1 GHz, $\varepsilon'$ is between 2 and 60 typically around 30 and $\varepsilon''$ is between 1 and 30 typically 5 and regarding the complex permeability of the absorbing material, $\mu'$ is between 1 and 30 typically 20 and $\mu''$ is between 2 and 30 typically 6 to 15. The cup shaped cavity 103, which may be referred to as a cavity is made of a conductive material. The absorbing material may be any material that dissipates EM energy, for example Eccosorb® MCS, GDS and BSR, which the specifications thereof are incorporated herein by reference. Optionally, the thickness of the one or more layers 104 is between about 0.1 millimeters (mm) and about 10 cm.

Optionally, the height of the cup shaped cavity 103 is between about 0.5 millimeters (mm) and about 10 cm. Optionally, the width of the opening 110 of the cup shaped cavity 103 is between about 0.5 millimeters (mm) and about 20 centimeters. Optionally, the opening width is set according to the transmitted and/or received frequency and/or the size or configuration of the EM element(s).

Optionally, the cup shaped cavity 103 comprises a plurality of chambers wherein in each chamber contains a different EM element, such as the EM element 101. The plurality of EM elements can also be used inside a single non-divided or partly chambered cavity.

The one or more layers 104 are applied, for example laminated, on the cup shaped cavity 103 and/or molded as cup sized and shaped to engulf the cup shaped cavity 103 without blocking the opening 110. The cup shaped cavity 103 is optionally shaped to have a cubical outline, a cylindrical outline, a dome outline, a pyramid outline, or a conical outline, each having an open base set for being in direct or indirect (for example, via intermediate substance) contact with a skin tissue of a monitored, diagnosed EM probed, and/or monitored user. Optionally, the cup shaped cavity 103 is made of a conductive material, such as metal. Optionally and respectively the one or more layers 104 has a respective outline.

Optionally, the one or more layers 104 are extended to increase the surface area of absorbing material which is found above the space between the skin area above a monitored intrabody target area and the EM probe 100.

Figure 2:
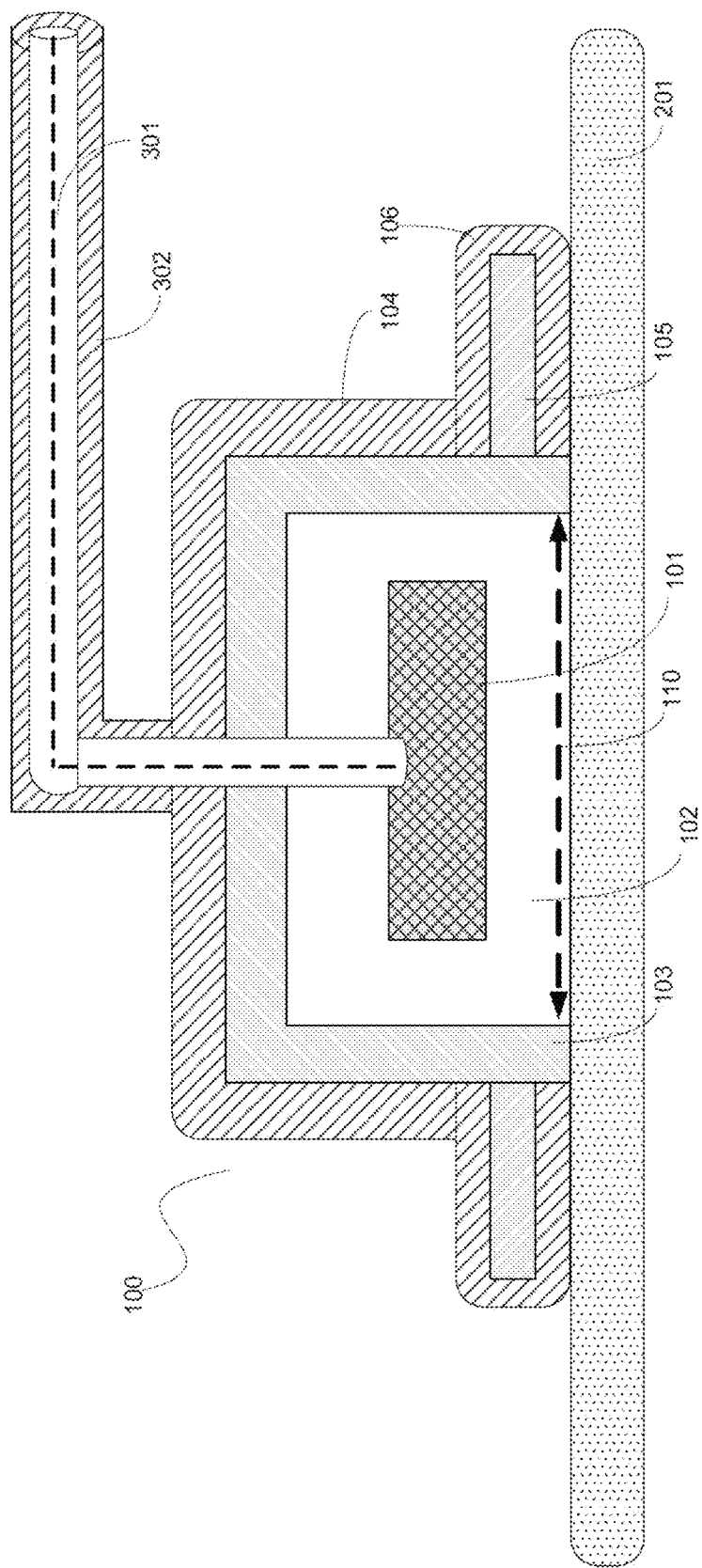
FIG. 2 is a schematic sectional illustration of an EM probe for monitoring at least one biological tissue having a circumferential flange, according to some embodiments of the present invention.

The EM probe 100 further includes one or more emitting and/or receiving elements 101 which are placed in the interior volume 102. Optionally, the EM radiation is radio frequency (RF) radiation and/or microwave (MW) radiation for example from a few 100 MHz's up to a few GHz. The emitting and/or receiving elements 101 are connected, by conducting element(s) 301, such as cables, for example coaxial cables, and/or waveguides, for example metal tubes used to carry microwave and/or RF energy with little loss of power, to external means for generating and/or analyzing EM signals, as further described below. The conducting element(s) 301 may be connected to the emitting and/or receiving elements 101 via an aperture in the lateral walls of the cup shaped cavity 103 and/or an aperture in the top wall of the cup shaped cavity 103, for example as shown in FIG. 2. As used herein, an emitting and/or receiving element means a transducer, an antenna, for example a bowtie antenna, an ultra-wide band (UWB) antenna, a micro strip antenna, a slot fed antenna, a dipole antenna, a patch antenna, and a spiral element antenna, a feedhorn and/or a tip of a waveguide which delivers and/or collects EM radiation. For example, in FIG. 1, an antenna is connected via a coaxial cable 301 to an external means for generating and/or analyzing EM signals (not shown).

Optionally, the interior volume 102 remains empty and therefore filled with air when being used. Optionally, the interior volume 102 is filled with a dielectric substance having a relatively high dielectric coefficient, for example about 10, such as Rogers R3010. Optionally, the dielectric substance has a dielectric coefficient which relatively matches the dielectric coefficient of body tissues or any matching material in-between. In such a manner, dielectric discontinuity is reduced and the efficiency of the transmission of the emitting element 101 and the sensitivity of the EM receiving element 101 is increased. Optionally, a layer of dielectric material, elastic, shape preserving or other, or a composition of different materials, such as a gel with or without dielectric increasing agents, for example metal oxides or fluids, and is applied between the EM probe and the skin area 201. Optionally separating the layer of dielectric material and the skin is a layer of a biocompatible material.

Reference is now made to FIG. 2, which is a schematic sectional illustration of an EM probe 100 for monitoring at least one biological tissue, according to some embodiments of the present invention. The EM probe 100 is similar to the one depicted in FIG. 1, however it further includes a circumferential flange 105 that is attached to the cup shaped cavity 103, in proximity to the opening 110, for example few millimeters above the opening edge, as shown in FIG. 2 or on the same plane of the opening edge, as depicted in FIGS. 3A-B.

The circumferential flange 105 is placed around the opening 110, optionally so as to be parallel to a skin area 201 in proximity to a monitored, EM probed, and/or diagnosed tissue(s) of a monitored user in proximity to the skin area 201 about implanted antenna. The circumferential flange 105 is made of a conductive material, such as metal. The circumferential flange 105, which is optionally a non-circular or circular metal ring, surrounds the opening and is electrically coupled, for example galvanically connected, to the cup shaped cavity 103. Optionally, the circumferential flange 105 is an integral part of the cup shaped cavity 103. For example the circumferential flange 105 is a portion of the cup shaped cavity 103 that is bended to be substantially in parallel or in parallel to the skin area of a monitored, EM probed, and/or diagnosed tissue(s) of a monitored user.

It should be noted that the EM probe 100 may be part of an intrabody implant, such as a subdermal implant. In such an embodiment, the EM probe 100 is sized and shaped to be placed between the tissues. In such an embodiment, the opening 110 may directly face a fat layer or a muscle layer. In such embodiments, the aforementioned structure of the EM probe 100 reduces currents that may develop on the tissue surface.

Figure 3A:
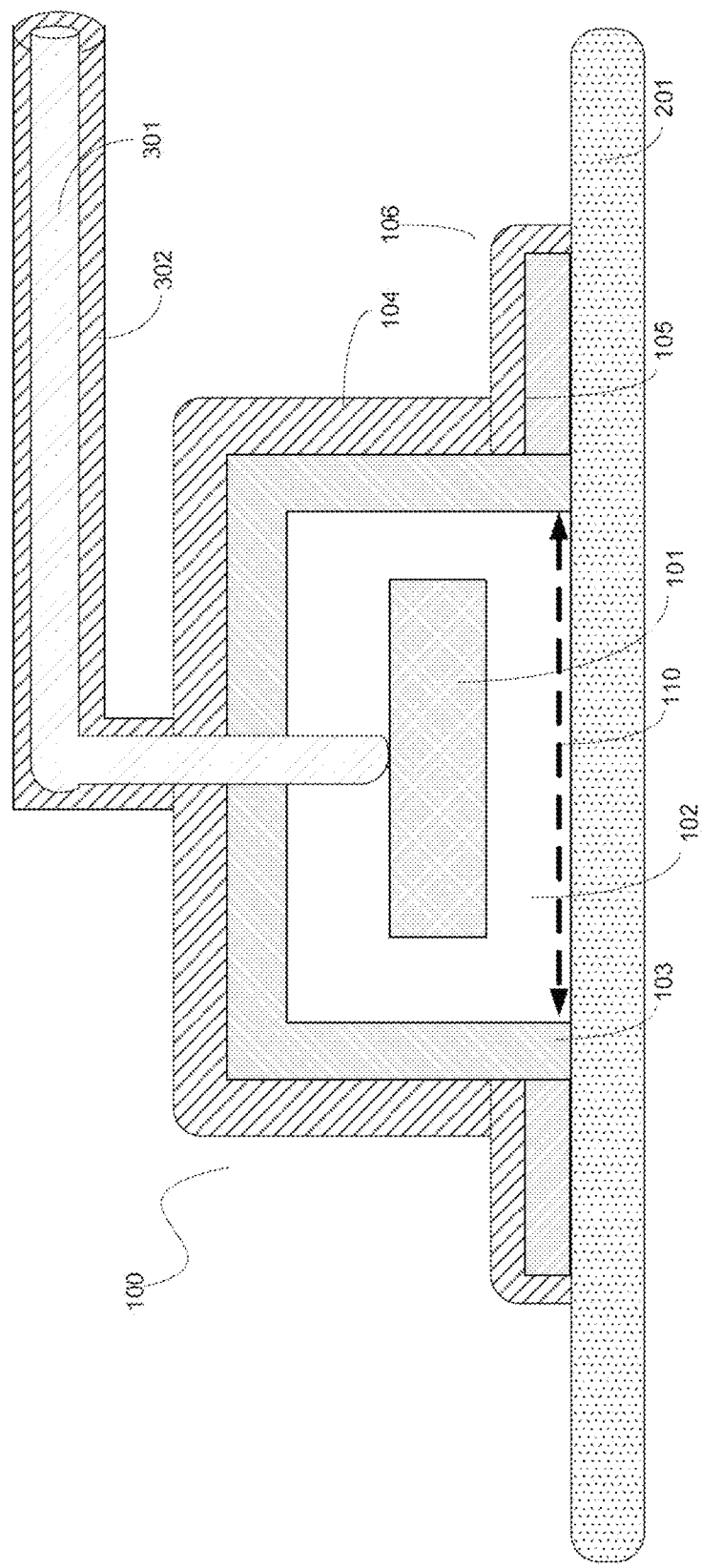
FIG. 3A is a schematic sectional illustration of an EM probe for monitoring at least one biological tissue having a circumferential flange, according to some embodiments of the present invention.
Figure 3B:
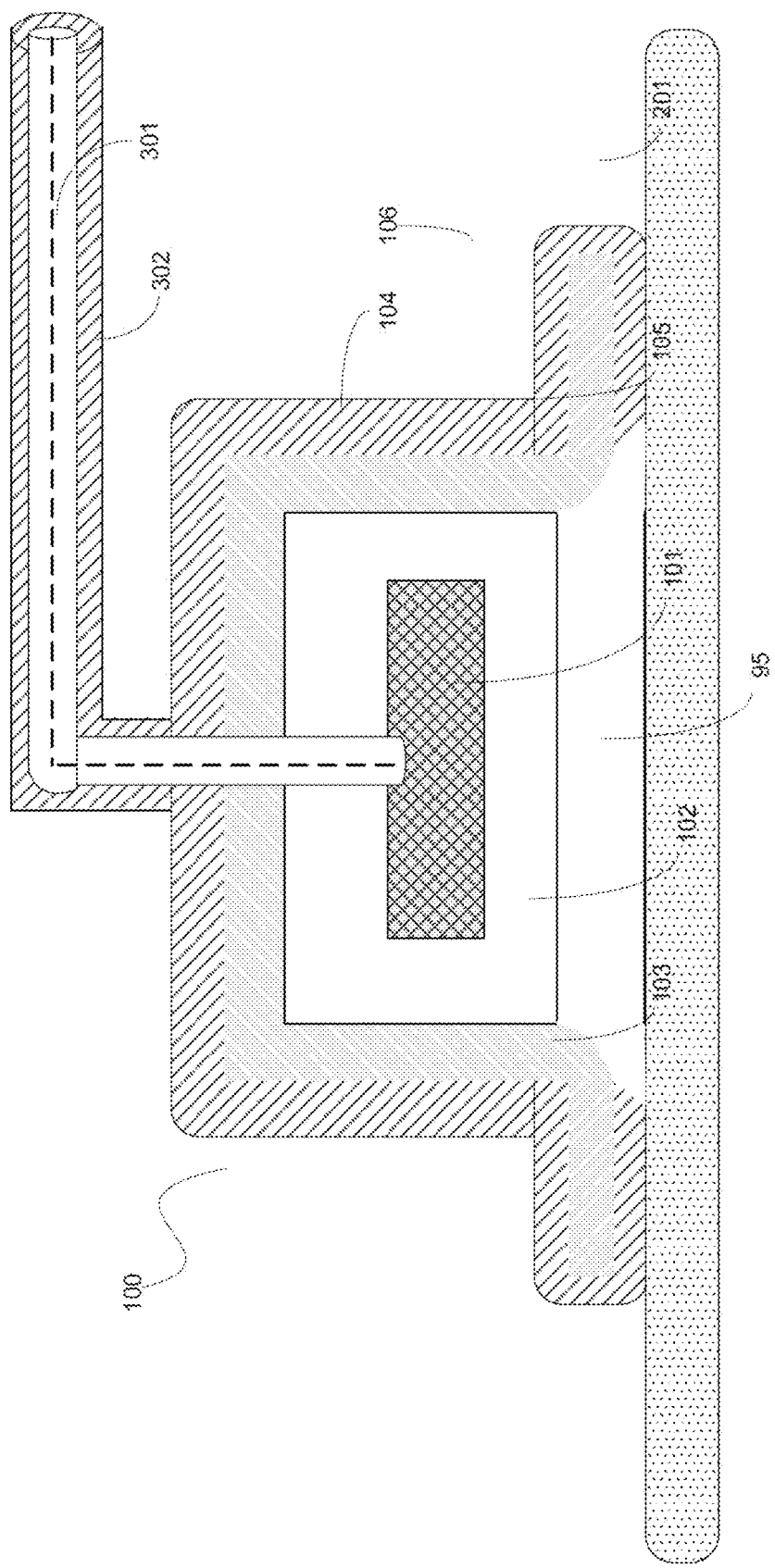
FIG. 3B is a schematic sectional illustration of an EM probe for monitoring at least one biological tissue having a circumferential flange, according to some embodiments of the present invention.

Optionally, the circumferential flange 105 is placed so that in use, the lower part thereof is in touch with or in a close proximity to the skin area 201, for example as shown at FIGS. 3A-B, or for instance via a cloth (i.e. a shirt, pants). Optionally, at least a portion of the circumferential flange 105 is covered by one or more layers of absorbing materials 106 which are in touch with or in a close proximity to the skin area 201. Generally and especially in the case where the EM probe is on top of a cloth, a construction similar to FIG.

3B can be used (at least the area marked with 95 is filled with air only). In this case, pressure is applied to the EM probe 100, for example by use of a chest strap, pushing it towards the body. The pressure applied on the depicted construction concentrates on the circumferential flange 105 and serves to improve mechanical coupling of the circumferential flange 105 to the skin area or, in the case of clothing reduce the gap, created by the layer of clothing.

Optionally, the portion is the edge of the circumferential flange 105, namely the area which is extended away from the cup shaped cavity 103. Optionally, the circumferential flange 105 is placed so that in use, the lower part of the one or more layers of absorbing materials 106 is in touch with or in a close proximity to the skin area 201. In the embodiment depicted in FIG. 2, the inner wire of the connected cable 301 is used for carrying signals intended to and/or received from the emitting and/or receiving elements 101, for brevity referred to herein as an EM element 101. Optionally, the EM element 101 is driven by a coaxial cable 301 whose inner wire and shield are connected to the EM element 101. Optionally, only the inner conductor is connected to the EM element 101. Optionally, the shield is connected and/or coupled to the cup shaped cavity 103.

The circumferential flange 105 conducts EM radiation originating from the cup shaped cavity 103 and/or from the interior volume 102 and/or from the skin area 201, facilitating its absorption in the layers of absorbing materials 106. Optionally, the circumferential flange 105 is continuous and annular. Optionally, the circumferential flange 105 comprises a plurality of separate elements which form a non-continuous and annular structure around the opening 110. Optionally, the circumferential flange 105 is continuous and planar.

The circumferential flange 105 increases isolation of the interior volume 102 from interference signals from areas and/or layers that are in the periphery of the EM probe and are superficial, for example the skin layer or fat layer, rather than from internal body tissues and/or organs that are of interest and are substantially in a region that is in front of the opening 110. The circumferential flange 105 effectually guides interference signals, such as close proximity parasitic EM radiation and/or currents traveling on the skin area 201, along the absorbing material 106 so as to dissipate them. In such a manner interfering effects may be reduced or eliminated. The interference signals are the radiation and/or currents which may be from the EM element 101, or from an area external to the EM probe, and travel along the body surface, for example on the skin 201 and/or via proximate subdermal tissues, such as fat and/or organs in close proximity to circumferential flange 105. The isolation of the interior volume 102 from interference signals may reduce the noise caused by parasitic signals originated from the EM transmission of the EM element 101 and/or from external interference signals which are not intercepted from the body of the monitored user. The isolation of the interior volume 102 also reduces the sensitivity to environment changes, such as hand movements or skin changes in proximity to the EM probe 100. In such a manner, for example, the effects of reflection signals originating from hand or other movements in the proximity of the EM probe and/or skin contour changes may be reduced.

Optionally, the distance between the peripheral outer edge of the circumferential flange 105 and the peripheral inner edge thereof is between 0.1 centimeters (cm) and 5 cm and/or a few wavelengths, for example 0.3 cm. Optionally, the circumferential flange 105 is placed, at least partly, inside the interior volume 102.

Figure 4:
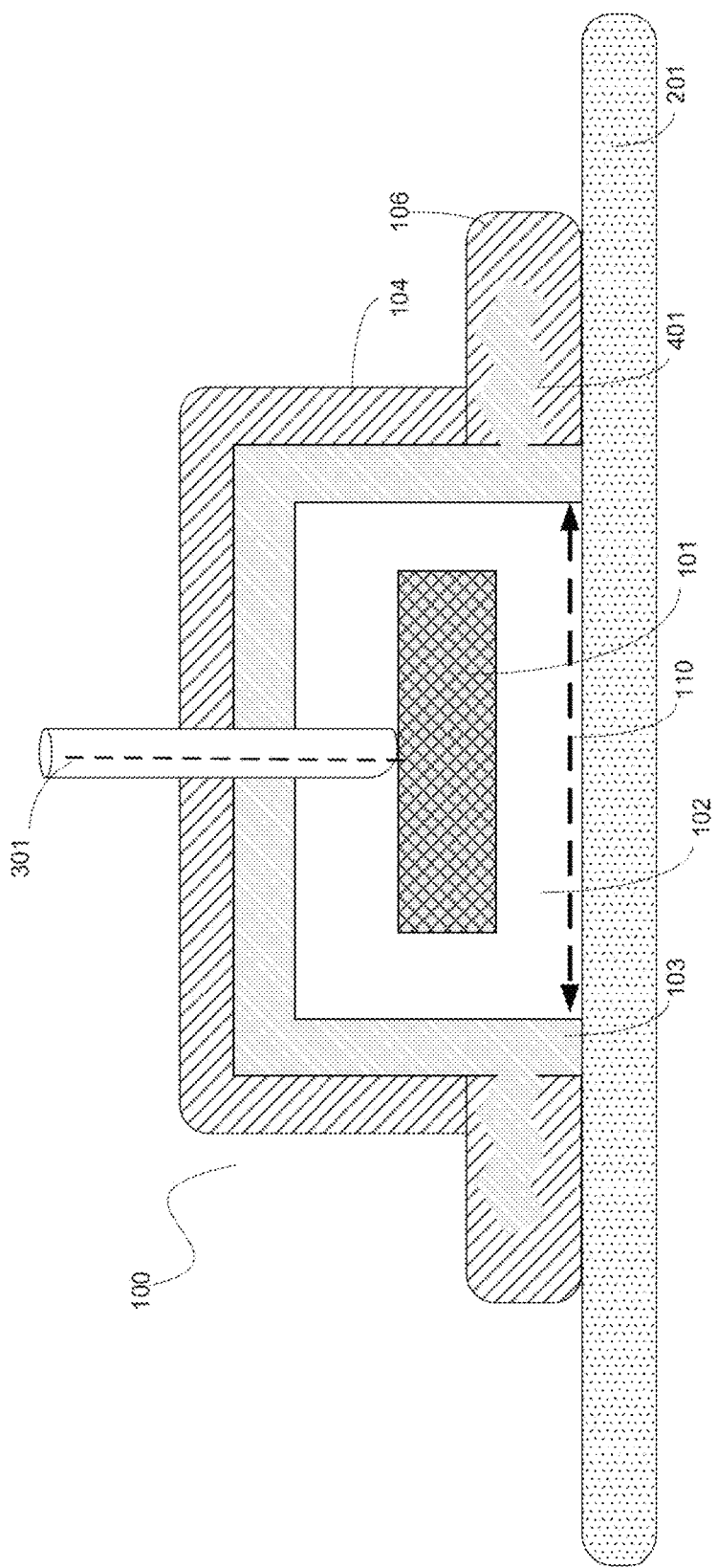
FIG. 4 is a schematic sectional illustration of an EM probe for monitoring at least one biological tissue having a zigzagged circumferential flange, according to some embodiments of the present invention.

Optionally, the circumferential flange 105 is substantially rigid. The larger the surface area of the circumferential flange 105, the higher is the isolation from interference signals. Since the isolation functionality of the circumferential flange 105 and the one or more layers of absorbing materials 106 are more effective when attached to the skin, optionally, at least some of the circumferential flange 105 and the absorbing material 106 which covers it are flexible so as to increase the surface area which is attached to the skin. Optionally, the circumferential flange 105 is substantially flexible, for example made of fiber based structures, flexible polymers, and/or a mesh having shape memory characteristics. This circumferential flange 105 may be bended in order to curve according to the surface of the skin area 201. Optionally, part of the circumferential flange 105 is rigid and part of flange 105 is flexible. In this case the flexible and rigid parts may be coupled or galvanically connected, and each part is coated with the absorbing material 106 separately or jointly. Optionally, the rigid portion is closer to the EM element 101 than the flexible portion, so the nearest volume to the EM element 101 is fixated and possibly pressed against the skin to decrease possible geometrical changes, for example of the skin and fat in proximity to the EM element. Optionally, the circumferential flange is jagged, zigzagged, curved, and/or bended along a plane parallel to the opening 110, for example shown in numeral 401 of FIG. 4. In such a manner, the path signals are passing along the circumferential flange 105 is longer so that their absorption is increased.

Some elements of the EM probe 100 are attached to the body of the monitored user, for example using adhesives, while others are disconnected therefrom.

According to some embodiments of the present invention, the circumferential flange 105 is set to enable an airtight interface between the EM probe 100 and the skin area, enabling attachment by air pressure differences. For example, a sub millimeter layer of silicon material is placed to cover the bottom side of the circumferential flange 105 and to form the airtight interface when attached to a skin area. The airtight interface may also increase the effectiveness of the isolation functionality of the circumferential flange 105 by improving the mechanical coupling of the circumferential flange 105 to the skin area. Optionally, a pressure regulator is attached to the cup shaped cavity 103 so as to control the air pressure in the inner volume of the cup shaped cavity 103. In such a manner, the air pressure differences may be controlled by the user and/or a clinician attaching the EM probe 100. In such an embodiment, the EM probe 100 is constructed to form an air gap above the opening 110. By reducing the air pressure in the gap, the attachment of the EM probe 100 to the skin area is formed. For example the gap created between the horizontal plane of the opening 110 and a plane thereabove in the cup shaped cavity 103. The lower pressure can be created by the pressure regulator, for example one or more one way valves connected to one or more pumps such as rubber balls. Another option is a mechanical lever that deforms the cup shaped cavity 103 after the attachment thereof to the skin area, substantially pulling back the dielectric material away from the skin creating a low pressure air gap.

According to some embodiments of the present invention, the circumferential flange 105 is a detachable element, set to be attached to a skin area above the monitored intrabody volume of the patient. In such an embodiment, the circumferential flange 105 may remain attached to the skin for durations of time in between different monitoring and/or diagnosis sessions, assisting in placement of the EM probe in following sessions. In addition, the ability to detach the cup shaped cavity 103 and optionally the EM element 101 which is mounted therein, allows, for example, cleaning the skin area between the sessions, replacing the cup shaped cavity 103 and/or the EM element 101 and/or repairing elements of the EM probe 100 without having to reposition or attach the circumferential flange 105.

Reference is now made to the isolation of the cable 301. In use, the edge of cable 301, which connects to the EM element 101, is typically close to the skin, parasitic EM radiation radiating from the skin area 201 and/or escaping from the cup shaped cavity 103 and/or originating from other sources may induce parasitic currents on the cable 301 that introduce noise. Optionally, a layer of an absorbing material 302, such as the aforementioned absorbing material, coats the cable 301 in proximity to the external surface of the cup shaped cavity 103. Optionally, the coating is along a portion of the cable 301, starting from the area in close proximity to the cup shaped cavity 103. This coating prevents from parasitic EM radiations which travel along the skin area 201 or passing through the air in proximity to the EM probe 100 from substantially affecting currents conducted by the cable 301 and/or substantially interfering with reception of the signals. This coating also prevents currents conducted on the cable from substantially radiating back into the same or other EM probes and/or their cables. This leakage might interfere with the operation of receiving signals from the monitored area in the body.

In some cases, a network of EM probes, each as shown at 100, is used for receiving and/or capturing signals from the monitored area in the body. In such an embodiment, the sensitivity of this network is greatly determined by the effect of crosstalk interference between the EM probes. Such crosstalk interference includes a reception of an EM signal that is transmitted from the network EM probes and does not propagate through an intended path. This EM signal might propagate on the skin, through air, or through cables or electronics connecting the EM probes, rather than through internal body tissues and/or organs. The crosstalk interference might interfere with the operation of the network and may also increase sensitivity to artifacts that are a result of body movements and changes in the surrounding. The aforementioned isolation isolates the EM probes from one another. Cables connecting the different EM probes might carry some of the signals on their outer shield and therefore should also be protected by the absorbing material as described herein. Moreover, the cables may operate as antennas transferring radiation and inducing currents on proximate cables. Currents induced on the cable of a receiving EM probe by radiation from a cable of a transmitting EM probe may penetrate into the internal volume of the receiving EM probe and therefore introduce noise. The crosstalk signal may be affected by movement of the cable or any respective movements between the cables increasing the overall noise in the system.

Figure 5:
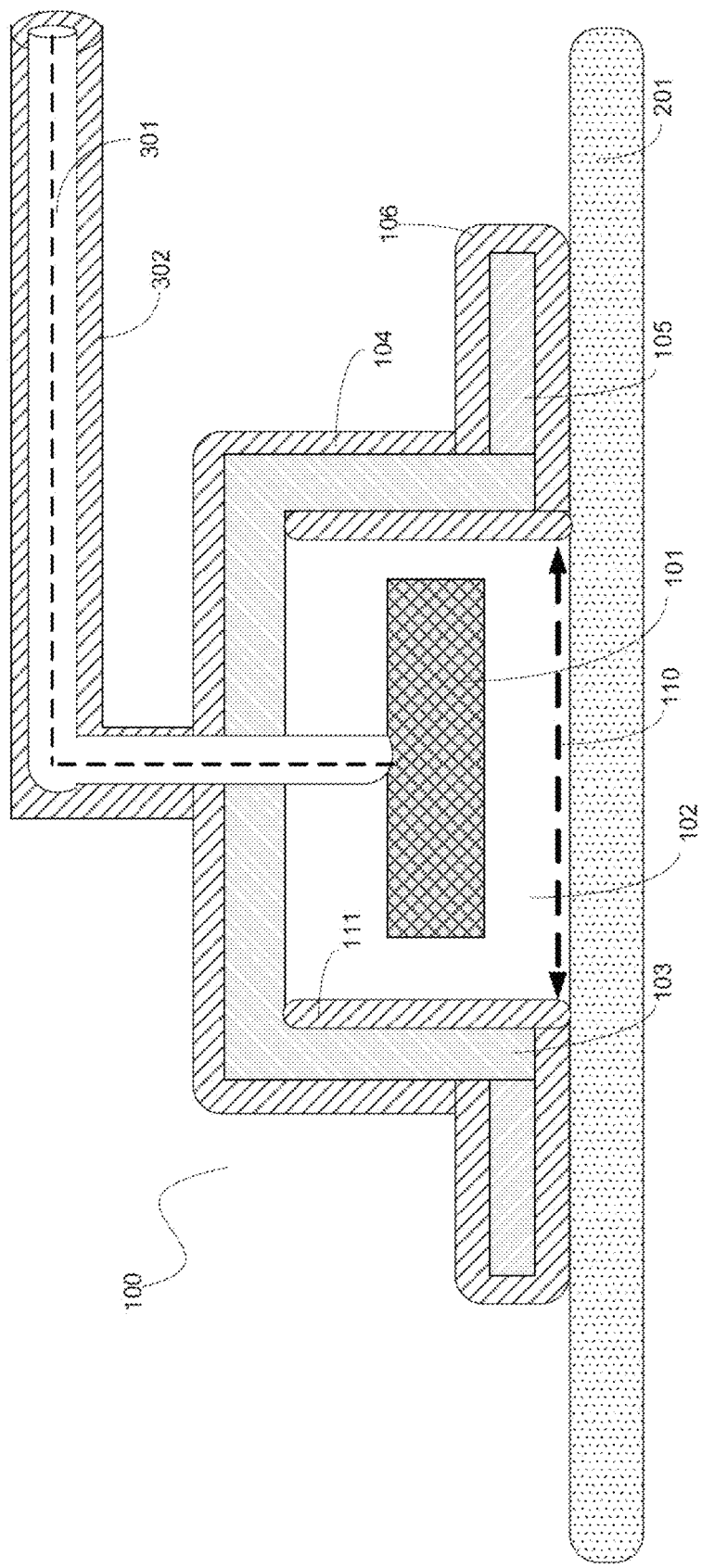
FIG. 5 is a schematic sectional illustration of an EM probe for monitoring at least one biological tissue having a cup shaped cavity with inner walls covered by one or more layers of absorbing materials, according to some embodiments of the present invention.
Figure 6:
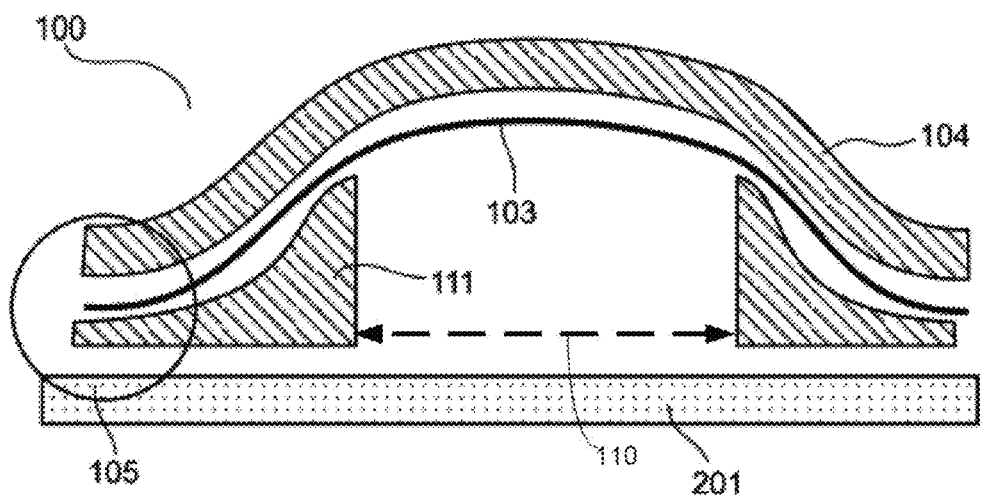
FIG. 6 is a schematic sectional illustration of an EM probe for monitoring at least one biological tissue having a dome shaped cavity, according to some embodiments of the present invention.

According to some embodiments of the present invention, some of the inner walls of the cup shaped cavity 103 are covered by one or more layers of absorbing materials, such as the aforementioned absorbing materials, for example as depicted by numeral 111 in FIG. 5. Optionally, the lateral walls of the cup shaped cavity 103 are covered with the aforementioned absorbing materials. Optionally, the lateral walls of the cup shaped cavity 103 and the circumferential flange 105 are covered with the aforementioned absorbing materials so that none of them touches the skin of the patient. Optionally, all the inner walls of the cup shaped cavity 103 are covered with the aforementioned absorbing materials. Optionally only the portions of the inner walls which are closer to the opening 110 are covered with the layers of absorbing materials 111. For example, FIG. 6 depicts a cup shaped cavity which is shaped as a dome. The circumferential flange 105 is encircled and marked with numeral 105. Optionally, only the inner wall of the cup shaped cavity 103 which faces the opening 110 remains uncovered by layers of absorbing material, for example as shown at FIG. 5.

It should be noted that layers 104, 106, 111 and 302 employ an absorbing material in proximity to conducting parts such as the cup shaped cavity 103, the circumferential flange 105 and/or the connected cable 301 so that parasitic EM signals and radiation traveling along these parts may be dissipated. In such a manner, interference signals, which propagate in close proximity to the EM element 101, are absorbed in one or more of the layers 104, 106, 111 and 302. The interference signals may be signals originated from the EM element 101, signals entering the interior volume 102 from the skin area 201, and/or straying signals which do not arrive from an intended path, i.e. parasitic signals.

According to some embodiments of the present invention, the EM element 101 is connected, via the cable 301, to a receiver and/or a transmitter which may be located in a different housing, for example in a mobile or a stationary unit, or within an element that is integrated with the EM probe, externally to the cup shaped cavity 103.

Optionally one or more attachment elements, as defined below, are used for attaching the EM probe 100 to the monitored user so that the opening 110 faces the skin area 201, for example as shown in FIGS. 1-4.

Figures 7A, 7B:
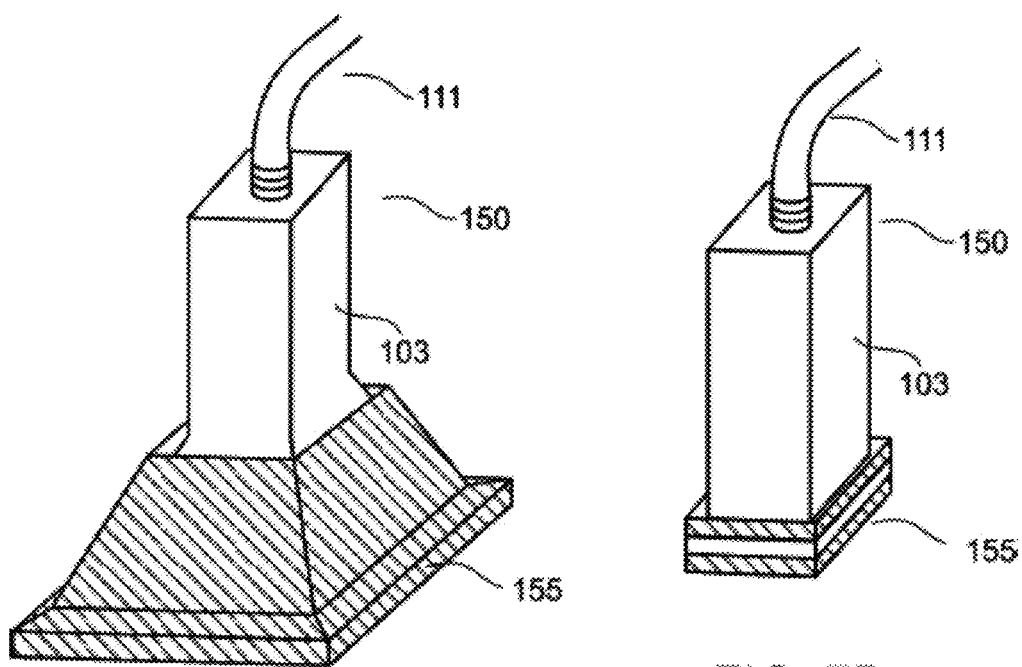
FIGS. 7A and 7B are schematic illustrations of an EM probe having an EM element placed outside of the interior volume of a cup shaped cavity, according to some embodiments of the present invention.

Reference is now also made to FIGS. 7A and 7B, which are schematic illustrations of an EM probe 150 having an EM element generating EM radiation, which is placed outside of the interior volume of the cup shaped cavity 103, according to some embodiments of the present invention. In such an embodiment, a conducting element, such as a waveguide, is used for conducting EM radiation, such as RF and/or MW waves which are generated outside of the cup shaped cavity 103 and conducted into the interior volume thereof. At least the lower portion of the circumferential flange around the opening is covered with an absorbing material 155, as described above. Optionally, also the external lower part of the cup shaped cavity 103 is covered with the absorbing material 155.

Figure 8:
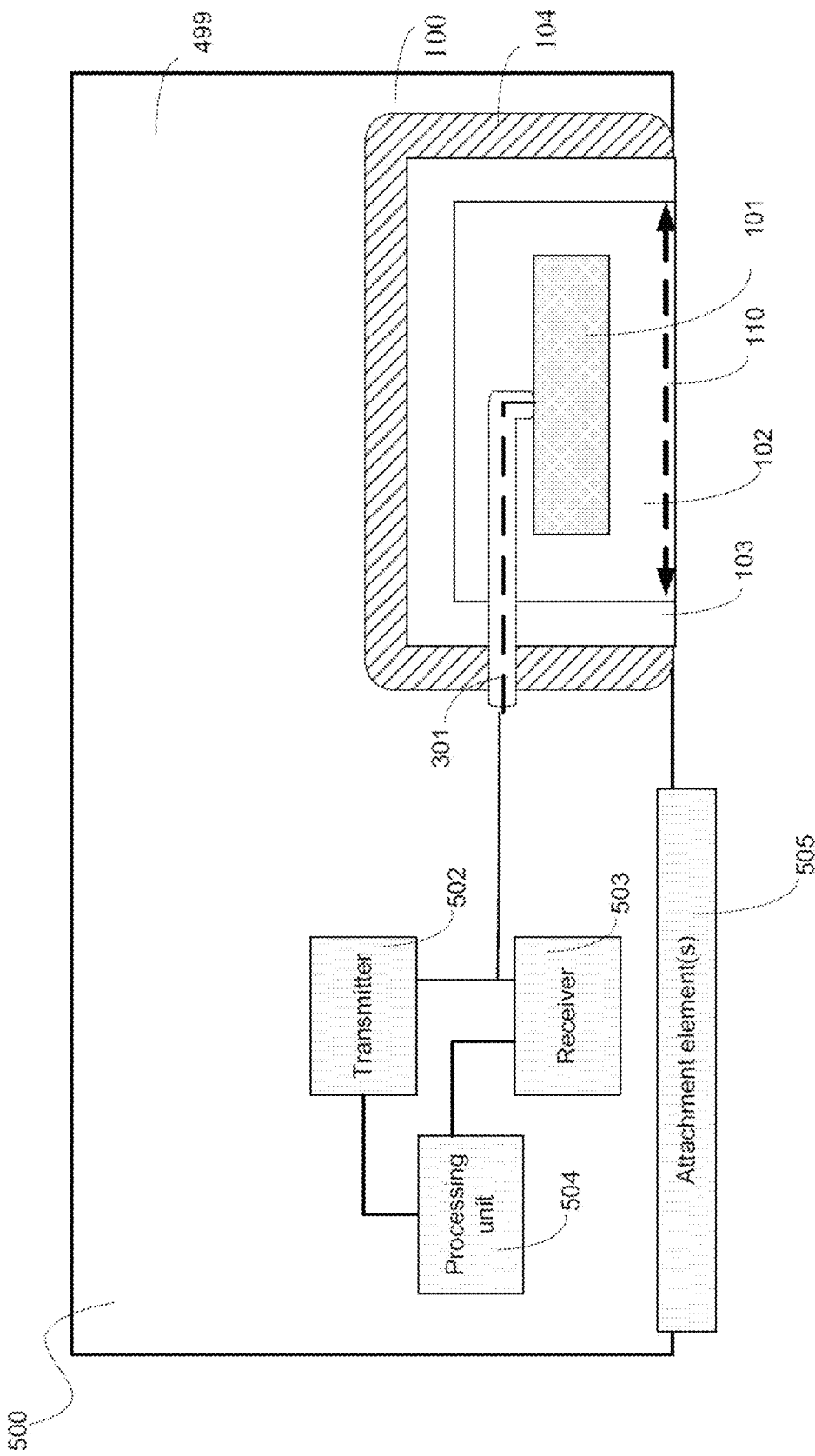
FIG. 8 is a schematic sectional illustration of a wearable device having an EM probe for monitoring at least one biological tissue, according to some embodiments of the present invention.

Reference is now made to FIG. 8, which is a sectional schematic illustration of a wearable device 500 for monitoring a biological tissue(s), according to some embodiments of the present invention. The wearable device 500 include a housing 499 which contains one or more of the EM probe 100 and one or more additional components for monitoring a monitored user, optionally ambulatory, and optionally for detecting one or more physiological patterns according to a dielectric property, for example as described in International patent application pub. No WO 2010/100649, International patent application pub. No WO 2009/031150, and/or International patent application pub. No 2009/031149, which are incorporated herein by reference. The dielectric property is calculated based on the reading of the EM radiation captured by the EM element. Optionally, a transmitter 502 is used to generate a signal that is transmitted to the EM element 101 for transmission. Optionally, a receiver 503 is used to receive a signal that is received by the EM element 101. Optionally, the processing unit 504 is a microprocessor or any other computing unit used to analyze the outputs of the receiver 503 and/or to control the transmitter 502. The processing is optionally performed as described in International patent application pub. No WO 2010/100649, International patent application pub. No WO 2009/031150, and/or International patent application pub. No 2009/031149, which are incorporated herein by reference. Optionally, the wearable device 500 includes one or more attachment elements 505, such as straps, coatings of adhesive. When straps are used, the wearable device 500 may be placed above a cloth (i.e. shirt, pants). Adhesive elements, and buckle components, for attaching the wearable monitoring apparatus 500 to the body of a monitored user with the opening 110 facing a skin area (not shown). In another embodiment of the present invention, such attachment elements 505 may be used for connecting only the EM probe 100 to the skin area. It should be noted that the components described in FIG. 8 may be part of a stationary system in which only the EM probe 100 is attached to the body of the monitored user.

Figure 9:
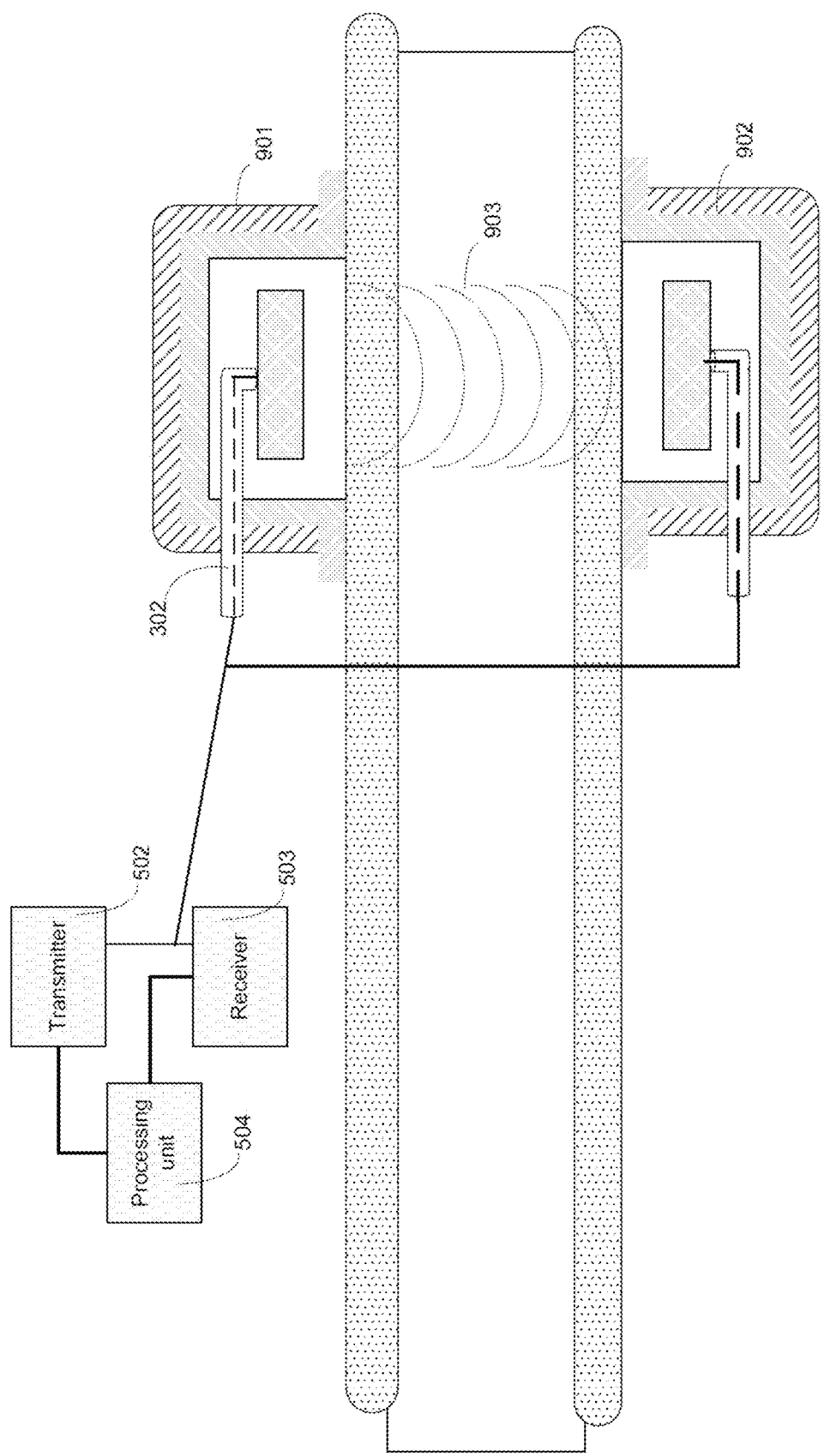
FIG. 9 is a sectional schematic illustration of a system for monitoring a biological tissue(s) by an analysis of passing through signals, according to some embodiments of the present invention.

Reference is now made to FIG. 9, which is a sectional schematic illustration of a system 500 for monitoring a biological tissue(s) by an analysis of passing through signals 903, according to some embodiments of the present invention. Components 502-504 are as depicted in FIG. 8, however in these embodiments at least two EM probes 901, 902 are used. One EM probe 901 is used for transmitting EM radiation toward a body organ or a number of body tissues and another EM probe 902 is used for receiving the passing through EM radiation 903. Optionally, the transmitting EM probe 901 is also set to receive reflections of the EM radiation from the body part. Optionally, the EM probe 902 is also set to transmit EM radiation toward the body part. Each one of the EM radiation EM probes 901, 902 may be defined as any of the aforementioned embodiments. In such an embodiment the intended path can be, for example, the path passing from EM probe 902 to EM probe 901. The isolation properties as described in the aforementioned may serve to minimize interference to the reception of EM radiation from this path.

Reference is now made to FIG. 10A, which is a sectional schematic illustration of a printed circuit board (PCB) EM probe 600 having a fabricated cup shaped cavity 601 and to FIG. 10B which is a three dimensional schematic illustration of this PCB EM probe 600, according to some embodiments of the present invention. The PCB EM probe 600 is created by a number of layers. As shown at 602, a layer of absorbent material, such as Eccosorb® MCS, is placed above a layer of conductive material 603, such as a metal layer. A stratified layer 620 below the conductive material 603 is constructed. The stratified layer 620 includes lateral walls 604, which are formed around a dielectric substance 608 having a relatively high dielectric coefficient, for example about 10, such as Rogers R3010, for example as described above. A conducting element 606, such as a wire, is placed in the dielectric substance 608, optionally in parallel to the layer of conductive material 603, and is extended outside the PCB EM probe through the lateral walls with no electrical connection to them. Another electrical connection (not shown) is possibly made and extended to the outside of the PCB EM probe, in a similar manner to the EM element 615 or to the fabricated cup shaped cavity. This allows connecting an EM element 615, such as an antenna thereto. In such a manner, an internal volume is formed contained within the reflecting walls 604 and the layer of conductive material 603.

According to some embodiment of the present invention the PCB EM probe 600 may be created by fabricating and bonding 4 layers, using fabrication techniques. For example, each layer is fabricated from a "blank PCB" made of a bonded metal, for example copper, and a substrate such as Rogers R3010. The metal on the "blank PCBs" are etched away and the layers are then bonded together. The layers in such an embodiment can be comprised of the following layers:
1) a first layer the top of the formed cup shaped cavity and underneath it a substrate,
2) a second layer an additional substrate and underneath an etched antenna and one or more conducting wires feeding it,
3) a third layer—an additional substrate and underneath it an etched peripheral circumferential flange, and
4) a fourth layer—a bare substrate layer with no metal.

These 4 layers are bonded together where the first layer is the topmost layer and fourth layer is the bottom layer. Optionally, the lateral wall(s) 604 are made by drilling dense via holes and filling them with a conductive material. Such dense via holes, optionally with metal connecting among them in each horizontal layer, may function as a metal plate for wavelengths greater than the distance between each pair of dense via holes. When such via holes are drilled in said substrate some dielectric material may remain effectively outside the cup shaped cavity due to fabrication limitations, for example 612 as in FIG. 10A. Optionally, the four layers are sized and shaped as in FIG. 10B. Optionally, a shaped absorbing material is bonded on the top of the created PCB EM probe and on the bottom side of the flange. Electronic circuitry like amplifiers, transformers, filters, receivers and transmitters, data collector and/or communication modules may be constructed between each pair of layers. For example, additional layers can be added on top of the cup and use the conductive upper part of the cap as a ground plane. This electronic circuitry can then be put inside an additional cavity. Various embodiments and aspects of the present invention as delineated hereinabove and as claimed in the claims section below find experimental support in the following examples.

In some embodiments of the present invention, an adhesive patch having a planar member which comprises in it at least one layer of radiation absorbing material may be used to attach an EM probe to the skin of a monitored user.

The radiation absorbing material may comprise any of the aforementioned absorbing materials and any combination thereof. Additionally or alternatively an absorbing material may comprise of or consist of one or more EM manipulating materials. As used herein, an EM manipulating material may mean a material that affects an EM wave and/or field propagation, for example by absorbing and/or dissipating energy, and/or by conducting, being resistive to, isolating, deflecting and/or attenuating EM energy.

Examples for EM manipulating materials include EM energy absorptive materials such as ferromagnetic materials and/or structures, and/or conductive materials coated with one or more layers of, for example, ferromagnetic material. In some examples the EM manipulating materials are in the form of or embedded in a fabric, for example a fabric comprising resistive fibers and/or strips and/or ferromagnetic material comprising fibers and/or conductive fibers coated and/or fibers coated with ferromagnetic materials. The EM manipulating materials are optionally layered, optionally set in sewed or bonded, for example by an adhesive, or otherwise connected in patches and/or strips and/or intertwined and/or embedded in one or more layers of the planar member.

EM manipulating material(s) may be taken to mean materials including or consisting of one or more of EM absorptive and/or restrictive and/or conductive materials, and/or resistive sheet and/or fabric, and/or materials having significantly higher permittivity and permeability than air, and/or materials having permittivity and/or permeability with high loss, and/or a construction of materials (or metamaterials) with different impedance for guiding the radiation away from inside body and/or on the periphery of the body.

In some embodiments, EM manipulating materials comprise metamaterials. Metamaterials may be structures or a combination of structures of metals or different materials with different permittivity and permeability with or without components with different inductance, reactance, and/or resistive properties integrated into them in a certain structure so as to implement desired impedance. It may comprise a network of resistors with capacitors and coils.

Examples for EM manipulating materials include materials having one or more of the following properties:

Permeability loss tangent of (tan $\delta = \mu''/\mu'$)>0.01 or >0.3 or >0.6 for all or some of the frequencies within the range of 100 MHz-5 GHz for example for 1 GHz and/or 2 GHz.

Permittivity loss tangent of (tan $\delta = \epsilon''/\epsilon'$)>0.01 or >0.3 or >0.6 for all or some of the frequencies within the range of 100 MHz-5 GHz for example for 1 GHz and/or 2 GHz.

Partial conduciveness manifested by a surface resistivity between 20 and 10,000 Ohm per square (Q/sq) and/or a volumetric resistivity which is >$10^{-3}$ Ohm meter ($\Omega$m). For example, resistive substrates and/or volumetric resistive materials may be constructed from and/or comprised of resistive wiring and/or conductive wires with or without lumped resistors, capacitors, and/or inductance elements.

Examples for EM manipulating materials include CobalTex™, which is a near field magnetic radio frequency (RF) shielding fabric of Less EMF Inc or Eccosorb™ of Emerson and Cuming Microwave Products. Examples for surface resistive EM manipulating materials includes Statitec™ of 20 ohm/sq or 1000 ohm/sq EMF Inc. and metallic materials, for example a metal foil. Resistive EM manipulating materials may be combined with near field magnetic RF shielding materials.

Additional examples include materials capable of diverting, reflecting disrupting and/or attenuating EM propagation.

Optionally, the EM manipulating materials includes materials which absorb electric fields and/or magnetic fields. Optionally the complex permittivity of such EM manipulating materials at a frequency of about 1 Ghz, $\epsilon'$ is between 2 and 60 or around 8-30 and $\epsilon''$ is between 1 and 30 or even 5-10 and regarding the complex permeability of the EM manipulating material, $\mu'$ is between 1 and 30 or about 20 and $\mu''$ is between 1 and 30 or even 6 to 15. The EM manipulating material may be Eccosorb® MCS, GDS and BSR, which the specifications thereof are incorporated herein by reference. Optionally, the thickness of the one or more layers and/or patches formed from of EM manipulating materials is between about 0.1 millimeters (mm) and about 5 mm.

Figure 14A:
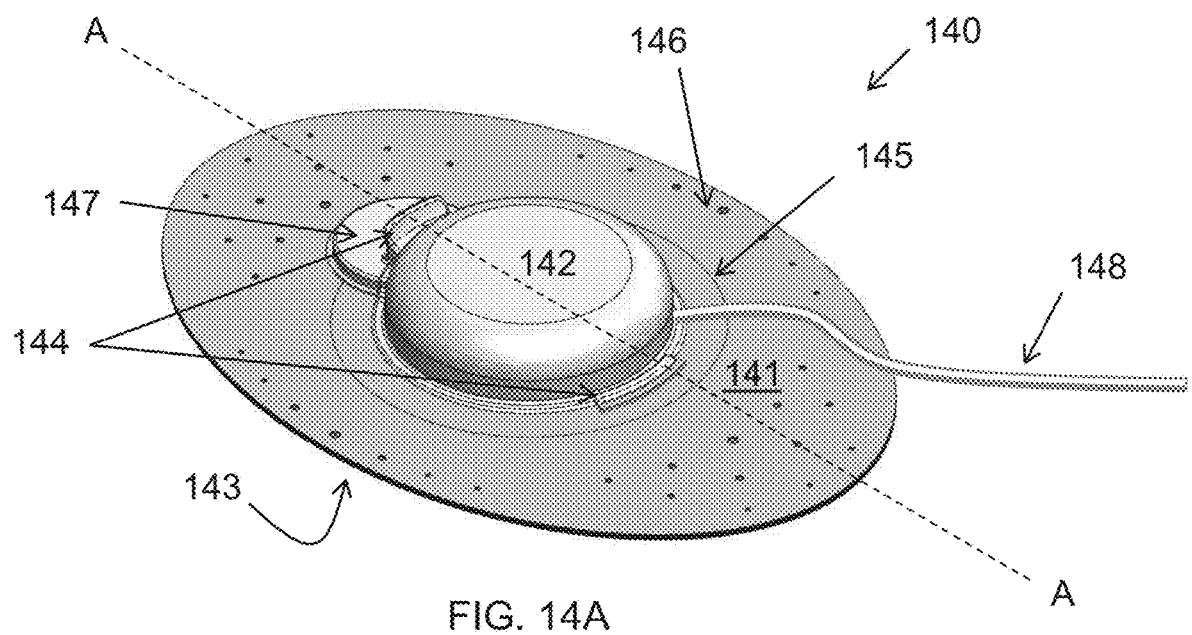
FIGS. 14A-14B depict schematic perspective views of adhesive patches for attaching at least one EM probe to a subject's body according to some embodiments hereof.
Figure 14B:
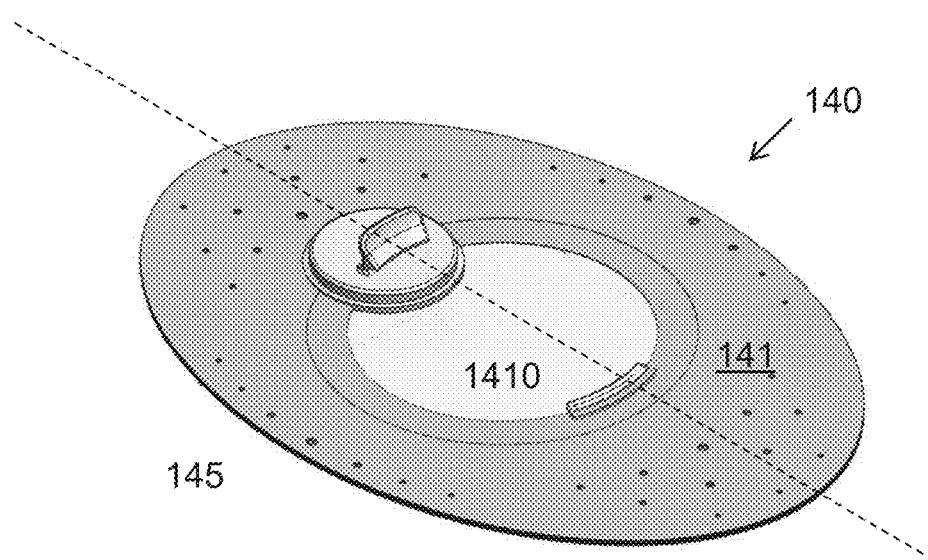
Figure 14C:
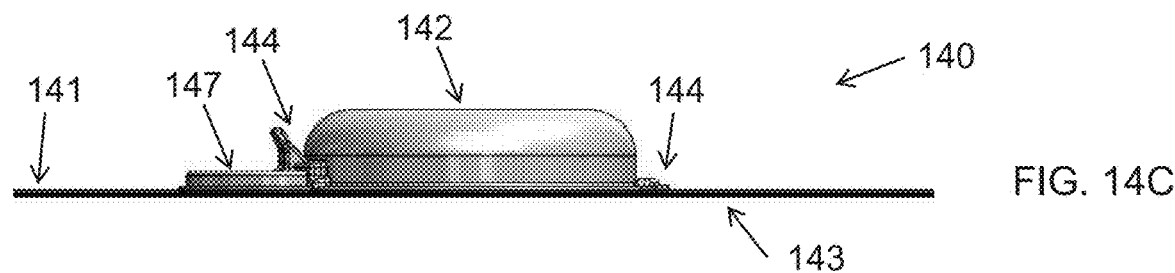
FIGS. 14C and 14D depict schematic lateral views of the adhesive patches shown in FIGS. 14A and 14B, respectively.
Figure 14D:
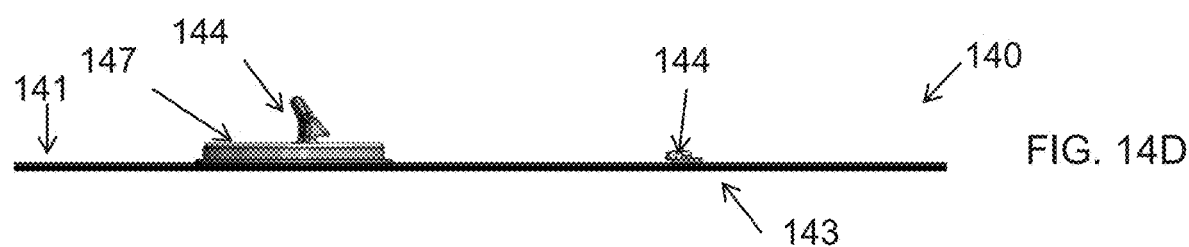

Attention is now drawn to FIGS. 14A-14D showing an example of some adhesive patches according to some embodiments hereof. FIGS. 14A and 14C, respectively, depict a schematic view and a lateral view of an adhesive patch 140 having a planar member 141 and an EM probe 142 attached thereto. FIGS. 14B and 14D, respectively, depict a schematic view and a lateral view of the adhesive patch 140 of FIG. 14A, with EM probe 142 removed.

Planar member 141 is manufactured comprising at least one layer of radiation absorbing material, and at least one layer 143 of an adhesive attached over at least part of a surface of the planar member, for attaching the adhesive patch to the skin of a user. This adhesive may be covered by a removable peelable liner that is peeled off before the adhesive patch 140 is to be attached to the skin of a user. At least one opening 1410 is formed within the at least one layer of radiation absorbing material to allow the propagation of EM radiation via the opening 1410 from one side of the planar member 141 to the other. In some embodiments, the at least one opening measures at least 1 cm in any direction parallel to the planar surface of the adhesive patch, and the adhesive patch extends by at least 1 cm around the opening in all directions parallel to the planar surface, for at least 75% of the circumference of the opening. In some embodiments at least one opening 1410 has such dimensions and/or shape and/or filling material that allow propagation of EM radiation via the opening from one side of the planar member to the other, where the EM energy is in the range of 300 MHz to 30 GHz or EM energy in the range between 400 MHz and 5 GHz or is within a range that its absorbed efficiently by the absorbing material in the adhesive patch. Optionally, opening 1410 has such dimensions and/or filling materials to allow EM propagation such that when an EM probe is attached to a human body (or a simulation of a human body) and transmits EM energy (in the range of 300 MHz to 30 GHz or EM energy in the range between 400 MHz and 5 GHz or is within a range that its absorbed efficiently by the absorbing material in the adhesive patch) to the body, and the energy is measured at a point 5 cm below the skin, the amount of energy that is measured when the probe is attached to the body via an adhesive patch according to some embodiments of the invention is at least 1% of the amount measured if the same transmission is performed without an adhesive patch. Optionally the opening area will have filling materials which have low EM absorption in the relevant frequencies, which filling materials may be or comprise medical adhesives, plastic and/or silicon materials. Optionally the opening has a shape and size that is about the same as the circumference of a flange to which the adhesive patch is to be attached or about the same as the inner circumference of the bottom of the opening of the EM probe or any size or shape therebetween.

As shown in FIGS. 14A and 14C, at least one EM probe 142 may be attached to planar member 141 above the at least one opening 1410, position to transmit and/or receive radiation via the opening. The opening 1410 may traverse planar member 141, including all its layers or it may traverse some of the layers, or even just the layer of radiation absorbing material. In some embodiments, opening 1410 is filled with, and/or positioned above or below, material that is EM radiation transparent. Such transparent material may be essentially limited to the region of opening 1410 or it may extend to other regions of adhesive patch 140. As used herein, a material is EM radiation transparent if it attenuates EM energy (e.g. in the range of 300 MHz to 30 GHz or between 400 MHz and 5 GHz) by not more than 20 dB. This may be measured, for example, within a human like body at 5 cm below the surface. Optionally the EM transparent material may be selected to match between the EM probe and the dielectrics of a user's body. For example, such matching material may have a dielectric coefficient above 3, for example between 3 and 20 (e.g. silicone or a silicone based material). The matching material may also be selected to be sufficiently elastic or pliable to conform to the contour of a user's body and fill the gap between EM probe 142 and the skin of a user.

In some embodiments, a plurality of openings 1410 may be formed in an adhesive patch 1410. A single EM probe 142 may be positioned to transmit and/or receive radiation via a plurality of openings 1410 and/or a plurality of EM probes 142 may be attached to a single planar member 141, for example, each above an opening 1410.

In addition, adhesive patch 140 comprises at least one mechanical connector 144 for connecting the at least one EM probe 142 to planar member 141 at a position at least partially overlapping the opening 1410. The connector(s) 144 may connect directly to connectors or matching structures on EM probe 142 or indirectly, for example via a housing to which EM probe 142 is attached. The arrangement and number of connector(s) 144 may be selected according to the number and/or arrangement of EM probe(s) 142 and opening(s) 1410 of the adhesive patch 140. The connector(s) 144 may be configured to ensure electrical connection between EM probe(s) 142 and any electrical connectors that might be included in adhesive patch 140 (e.g. for a battery 147 as detailed hereinafter).

The connector(s) 144 may be constructed in any manner known in the art for mechanically connecting to a matching structure or connector on the EM probe and/or on a housing or cover connected to the EM probe. The connectors may allow locking the EM probe in position so that it may not detach unintentionally from the adhesive patch. The connectors may snap and/or latch and/or bond (e.g. when a connector is or comprises an adhesive) and/or interlock and/or lock one to the other, for example pressing connectors and/or snapping and/or twisting them one with respect to the other, etc. One or more of the matching connectors be formed of and/or may have in them additional grooves and/or indentations and/or protrusions for securing the EM probe(s) and adhesive patch in a locked position. Optionally, the connectors allow positioning the EM probe 142 at a one or a plurality of selected orientations or positions overlapping opening 1410.

In the example shown, planar member 141 is bendable and/or a flexible, to the extent that it may conform to the skin surface of a monitored user and to a user's body contour at that area. Optionally, planar member has an essentially planar surface only at the bottom thereof for contacting the skin. Optionally, the planar surface of planar member 141 includes grooves and/or is zigzagged, jagged, and/or curved to extend the path of signals passing therethrough.

In some embodiments a rigid member 145, the outline of which is shown in FIGS. 14A and 14B, may be included in planar member 141 (or attached thereto) and connected, directly or indirectly, to connector(s) 144. Rigid member 145 may serve to impart rigidity at the site where the EM probe 142 is attached to the planar member 141. Optionally, rigid member 145 is, at least partially, an integral part of connector(s) 144. Optionally, rigid member 145 serves as a mechanical connector or part thereof by virtue of providing support to the attachment of an EM probe 142 to adhesive patch 140 by an adhesive.

Optionally, rigid member is a closed shape as the ring formation as shown or unclosed (e.g. U shape) or even segmented shape or a combination thereof. Rigid member 145 is not limited to the round shape as shown and may have any other shape (e.g. elliptical, square, rhomboid, one or more arcs, etc.). Optionally, connector(s) 144 and/or rigid member 145 are made of or comprise a conductive material coated with an absorbing material. Optionally may comprise or consist of a plastic (e.g. PVC, polycarbonate, etc.). Optionally, connector(s) 144 and/or rigid member 145 may be sized and shaped so as to form an extension of the flange of the EM probe. Examples for such materials include metal sheets coated with a ferromagnetic absorber and plastics with/without layers of absorbing, resistive and/or conductive materials or fabrics.

Optionally, connectors 144 (alone and/or together with rigid member 145) are configured to attach EM probe 142 to planar member 141 in such manner so as to materially reduce or even prevent emission of EM radiation via the interface when the EM probe 142 and planar member 141 are attached to the skin of a user.

Optionally, adhesive patch 140 comprises a battery 147 for providing energy to EM probe 142, when in use. EM probe 142 may be connected, additionally or alternatively, to at least one wire 148 to receive power and/or for communication purposes, for example with one or more controllers and/or a processors and/display units. This wire may, in some embodiments, be provided as part of adhesive patch 140 or otherwise be connected thereto or be provided together with EM probe 142. In some embodiments, wire 148 may be integrated into adhesive patch 140 or attached thereto above the planar member 141, below adhesive layer 143 or in between the adhesive patch layers.

In some embodiments, adhesive patch 140 comprises perforation 146 through one or more, or all layers thereof, to allow a degree of ventilation for the skin under the adhesive patch, when in use.

In some embodiments, the adhesive patch is a disposable unit. In use, an EM probe 142 is removably attached to the adhesive patch 141 via connector(s) 144. After use, adhesive patch 140 may be discarded, while EM probe 142 may be reused with another adhesive patch for the same or another user.

In some embodiments, the adhesive patch is configured for multiple uses, meaning that one or more EM probes may be attached to the adhesive patch and detached therefrom in sequence, optionally while the adhesive patch remains attached to the skin of a user. In some embodiments this may be performed by virtue of connectors that can be connected and detached a plurality of times. In some embodiments this may comprise use of a plurality of single use connectors (e.g. patches of adhesive) that are used in sequence (e.g. for every use another layer of adhesive is exposed).

Optionally, the adhesive patch and/or a battery associated with the adhesive patch and/or the EM probe and/or a system component associated with the EM probe may include an adhesive patch authorization and activation module which is configured for identifying and authenticating an adhesive patch before an EM probe attached to the adhesive patch is allowed to be activated and/or enabled for activation and/or a warning is issued (for example to a user) in case of recognition of a lack of authorization. Authentication can be based for example on unique information stored in association with the adhesive patch. Authentication may serve for example to ensure that the size and/or shape of an adhesive patch and/or it's specific composition are compatible with an intended use or location (e.g. based on shape and/or size of the site to which an adhesive patch is to be attached) or a specific user (e.g. skin sensitivity) or a match between a battery and the EM probe which it should power, and/or to ensure a match between the radiation absorbing material and the radiation to be emitted by an EM probe Authentication information may be valid for a limited duration and/or number of activations. Such a module reduces fraud where a non-original adhesive patches that may be used within the system.

Figure 15A:
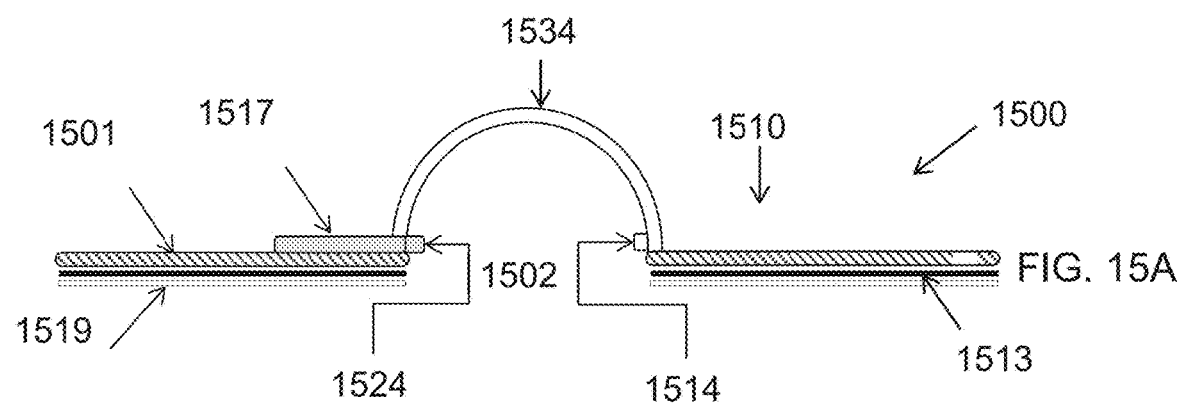
FIGS. 15A and 15B depict schematic cross sectional views of adhesive patches for attaching at least one EM probe to a subject's body according to some embodiments hereof, with and without an integral antenna cover, respectively.
Figure 15B:
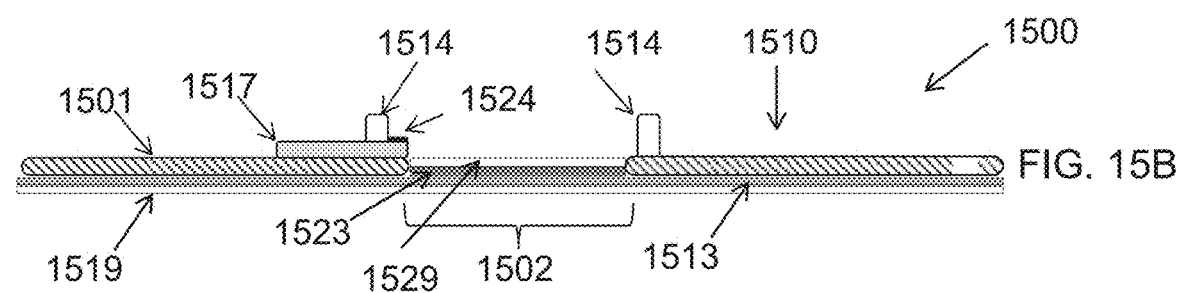

Attention is now drawn to FIGS. 15A and 15B, depicting lateral cross sections through an adhesive patch, essentially along a line at the position of line A-A shown in FIGS. 14A and 14B. If FIG. 15A adhesive patch 1510 is shown. Adhesive Patch 1510 is shown having a schematic mechanical connector 1514 for holding an EM probe (not shown) under cover 1534. Cover 1534 may comprise one or more connectors in addition to or instead of connector 1514. In some embodiments of this example, an EM probe may snap into location by being inserted from below the adhesive patch and clicking into contact with cover 1534.

Also visible is an optional battery 1517, having an electrical connector 1524 (e.g. pads) for electrically connecting battery 124 to an EM probe, once in position under cover 1534. Such connection may be configured to ensure a water tight interface between the electrical components in the probe and those that are on the patch (for example by associating rubber or silicone or another water sealing material with the EM probe and/or the adhesive patch). The electrical connector may comprise wires that are attached to or interwoven in planar member 1510 (e.g. in one or more of the layers and/or in-between layers) and are positioned to connect battery 1517 to an EM probe, when in position. In some embodiments, battery 1517 is a planar battery and is optionally interwoven in planar member 1510. In some embodiments, battery 1517 may be positioned in or attached to or otherwise integrated with cover 1534.

In this cross section planar member 1510 is shown to comprise a layer of radiation absorbing material 1501, an adhesive layer 1513 (in black) and a removable peelable liner 1519 under the adhesive. In this cross section, opening 1502 is shown to traverse all shown layers.

Alternatively, one or more layers other than radiation absorbing layer 1501 may extend under opening 1502, for example as shown in FIG. 15B. In this example, opening is flanked or surrounded by one or more mechanical connector(s) 1514. Adhesive layer 1513 covers, at least a part of the bottom surface of adhesive patch 1500, including at least a portion of the adhesive patch surface that is located under opening 1502. In some embodiments, and additional adhesive layer 1523 may be provided under or within or above opening 1502 to allow attaching an EM probe to a top surface of the planar member 1510 of adhesive patch 1500 at the region of opening 1502. In the shown example a removable peelable liner 1529 is positioned above adhesive layer 1523 and is to be removed to expose the adhesive for use.

Figure 16A:
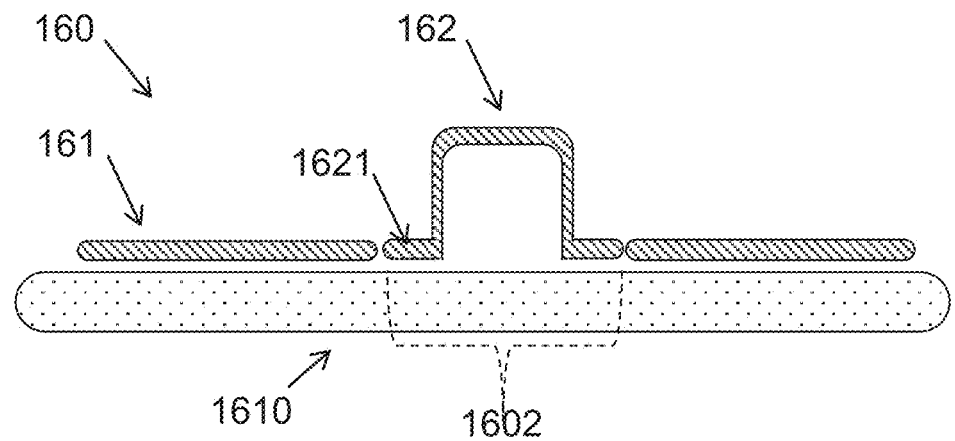
FIGS. 16A to 16C show schematic cross sectional views of adhesive patches, each having an antenna having a circumferential flange attached thereto, according to some embodiments of the invention.
Figure 16B:
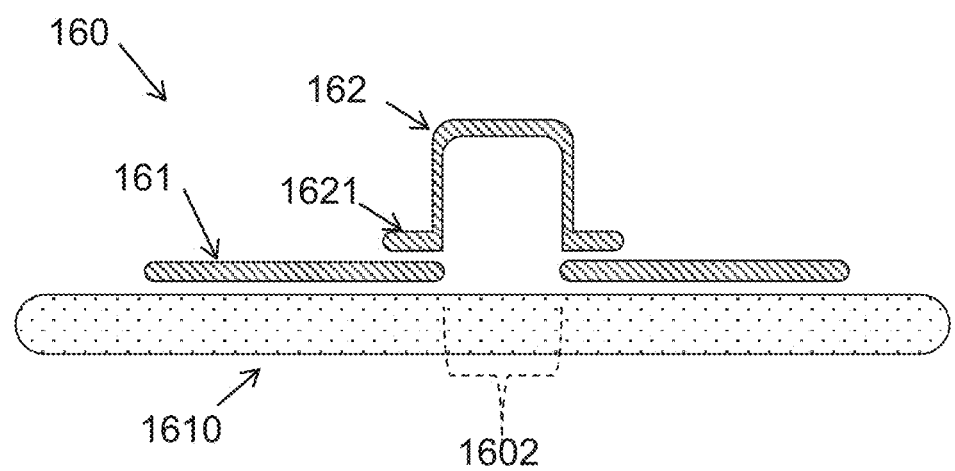
Figure 16C:
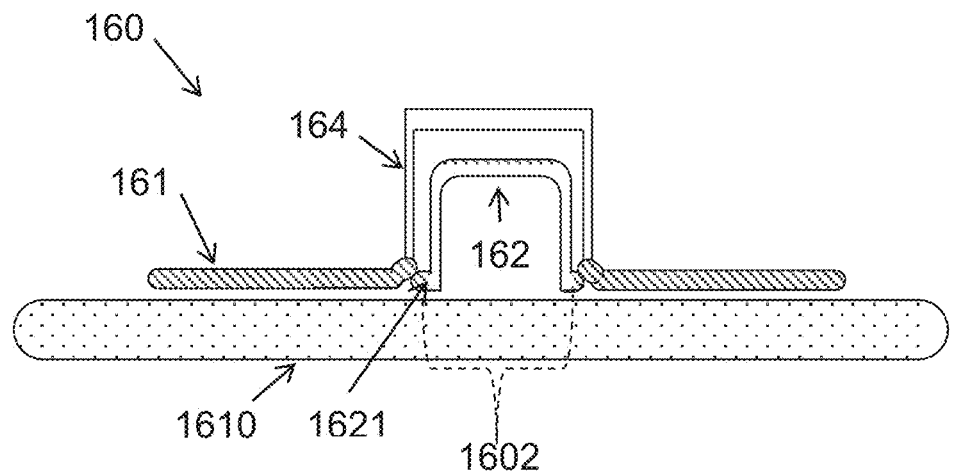

An adhesive patch according to some embodiments of the invention may provide an extension for a layer of radiation absorbing material covering the bottom side of circumferential flange of an EM probe. Some examples for the respective positioning of an EM probe having a flange and the radiation absorbing layer (or the entire planar member) of an adhesive patch according to some embodiments of the invention are depicted schematically in FIGS. 16A-16C. In FIGS. 16A-16C, EM probe 162 is shown attached to adhesive patch 160 atop the skin 1610 of a user. In cross section, EM probe 162 is depicted solely as a cup shape having a circumferential flange, positioned adjacent opening 1602. In some embodiments, EM probe is an EM probe as described above. As seen if the figures, planar member 161 may be essentially at the same level as flange 1621 For example—flange 1621 may touch the edge of opening 1602 or a gap may be bridged by a connector. Alternatively, flange 1621 may be positioned atop planar member 161 (FIG. 16B) or under planar member 161 (FIG. 16C). In FIG. 16B, flange 162 may be attached to the surface of planar member 161 (directly or indirectly) via one or more connectors and/or by an adhesive included in the adhesive patch 160 (as a top layer, possible below a removable layer) and/or on the bottom surface of the flange 1621. Additionally or alternatively, a cover (for example cover 164, as shown in FIG. 16C) may be included in adhesive patch 160 to cover and/or facilitate the attachment and/or positioning of the EM probe 162 to the adhesive patch 160.

Figure 17A:
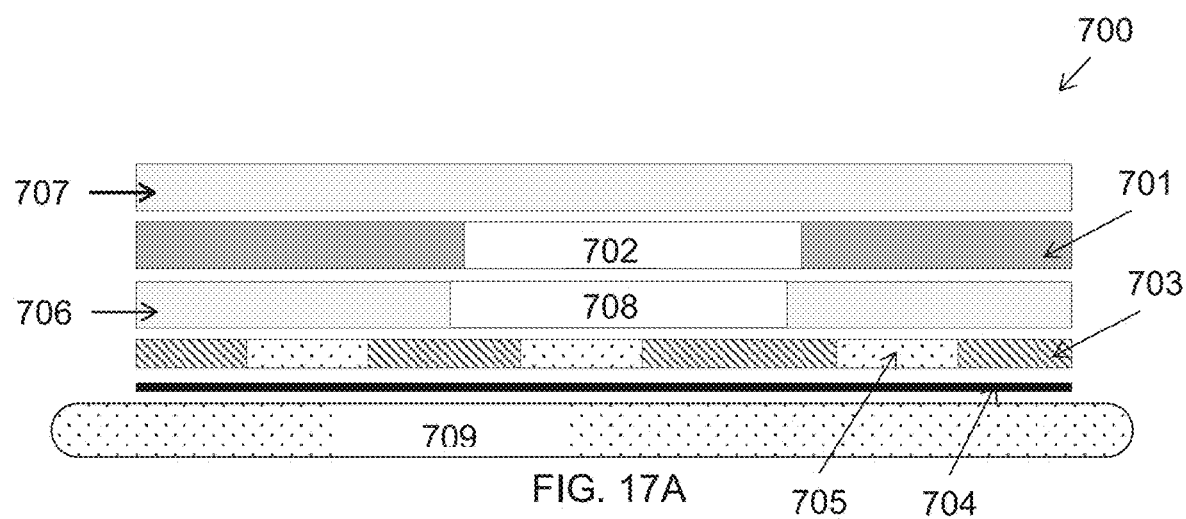
FIGS. 17A and 17B schematically depict cross-sections through a planar member of an adhesive patch according to some embodiments of the invention, the cross-section showing a plurality of layers comprised in the planar member.

Attention is now drawn to FIG. 17A, depicting a schematic vertical cross-section through a planar member 700 of an adhesive patch according to some embodiments of the invention, positioned over the skin 709 of a user. This cross-section shows a plurality of layers that are attached and/or fused and/or bounded together, for example by use of an adhesive or by sewing or otherwise.

In this example, planar member 700 comprises a radiation absorbing layer 701 comprising radiation absorbing material, within which an opening 702 is depicted. As detailed above, opening 702 may be empty or may comprise material that would not prevent the propagation of EM energy from one side of the planar member 700 to the other (for example, between the user's body and an EM probe attached to the adhesive patch; for example an attenuation of 20 dB or less).

Planar member 700 also comprises at least one adhesive layer 703, for attaching the adhesive patch to a user (e.g. directly to a user's skin). This layer may be continuous or discontinuous and may cover the entire surface on which it is applied or a portion thereof and/or be applied to form a pattern on the surface of planar member 700. In the example shown in FIG. 17A, the layer of adhesive layer 703 covers a portion of the bottom surface of planar member 700. In between areas having adhesive layer 703 are adhesive-free portions 705, which may be left empty or comprise a skin soothing material. Adhesive layer 703 may consist of or comprise an adhesive approved for medical or surgical purposes, for example an adhesive made of or comprising acrylate.

Below adhesive layer 703 or at least below the adhesive-covered portions thereof, may be a peelable liner 704. This layer may be selected to protect adhesive layer 703 form unintentionally sticking to materials before use. Any type of peelable liner that is compatible with the adhesive may be used, for example as known in the art for adhesive medical tape or bandages. For example, ploy-coated Kraft paper, or bleached Kraft paper, optionally silicone coated.

Planar member 700 may further comprise, above and/or below adhesive layer 703, one or more fabric layers 706 and 707 comprising or consisting of any type of woven fabric or non-woven fabric, plastic, or latex rubber, for example as materials known in the art for use in the manufacture of adhesive medical tape or bandages. These layers may span the entire surface or planar member 700 (as depicted schematically in fabric layer 707) or one or more parts thereof (as depicted schematically in fabric layer 706, having a gap 708 under opening 702).

In some embodiments, a commercially available adhesive tape may be used, to provide a fabric layer 706, adhesive layer 703 and liner 704. For example, 3M™ Medical Nonwoven Tape (Catalogue No. 1776) or 3M™ Elastic Medical Tape (Catalogue No. 9907W) (both from 3M Medical Specialties, USA). To this material at least one radiation absorbing layer 701 may be attached, for example by use of an adhesive or by sewing.

Finally, additional layers and/or material (not shown) may be included in a planar member 700 and/or attached thereto. Non-limiting examples include electrical wiring and/or a battery and/or battery components and/or electrical and/or mechanical connectors that may be attached directly or indirectly to planar member 700 (for example such as shown for wire 148 in FIG. 1) and/or embedded in one or more layers and/or between two or more layers of the planar member 700. In some embodiments, planar member 700 may comprise an adhesive coated portion or layer and a removable liner also at its top surface (being remote from the skin), positioned to serve as a connector for attaching one or more additional components (e.g. an EM probe and/or a connector or and/or a cover and/or a battery) to planar member 700.

In some embodiments, planar member 700 or one or more layers thereof, further comprises components that may impart rigidity to at least part of the planar member. In some embodiments planar member 700 is constructed such that it is more rigid and/or less flexible in regions that are closer to opening 702 than it is in regions that are closer to the periphery of the planar member 700.

Figure 17B:
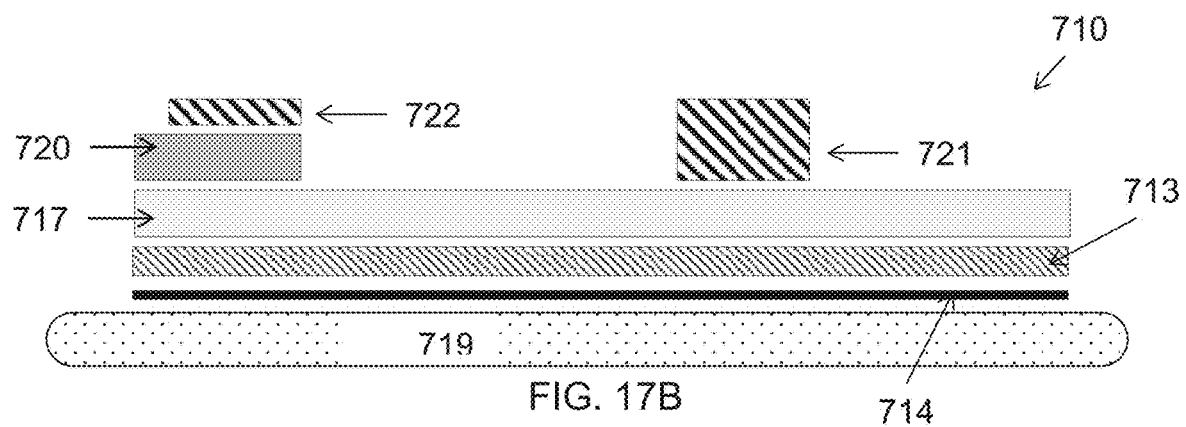

Attention is now drawn to FIG. 17B, depicting a schematic vertical cross-section through a planar member 710 of an adhesive patch according to some embodiments of the invention, positioned over the skin 719 of a user. This cross-section shows a plurality of layers that are attached and/or fused and/or bonded together, for example by use of an adhesive or by sewing or otherwise.

As shown, planar member 710 is optionally attached to a battery 720 (shown schematically). Optionally, planar member 710 is attached to one or more mechanical connectors 721 and 722 for attaching an EM probe (not shown) to the planar member 710. Battery 720 comprises an electrical connector allowing it to connect to an EM probe and provide power thereto.

Optionally, planar member 710 also comprises a radiation absorbing layer having an opening as described above in the context of FIG. 17A.

Planar member 710 also comprises at least one adhesive layer 713, for attaching the adhesive patch to a user (e.g. directly to a user's skin). This layer may be continuous as shown or discontinuous (as shown in FIG. 17A) and may cover the entire surface on which it is applied or a portion thereof and/or be applied to form a pattern on the surface of planar member 710. Adhesive layer 713 may consist of or comprise an adhesive approved for medical or surgical purposes, for example an adhesive made of or comprising acrylate.

Below adhesive layer 713 or at least below the adhesive-covered portions thereof, may be a peelable liner 714. This layer may be selected to protect adhesive layer 713 form unintentionally sticking to materials before use. Any type of peelable liner that is compatible with the adhesive may be used, for example as known in the art for adhesive medical tape or bandages. For example, ploy-coated Kraft paper, or bleached Kraft paper, optionally silicone coated.

Planar member 710 may further comprise, above and/or below adhesive layer 713, one or more fabric layers 717 comprising or consisting of any type of woven fabric or non-woven fabric, plastic, or latex rubber, for example as materials known in the art for use in the manufacture of adhesive medical tape or bandages. These layers may span the entire surface or planar member 710 (as depicted) or one or more parts thereof.

In some embodiments, a commercially available adhesive tape may be used, to provide a fabric layer 717, adhesive layer 713 and liner 714. For example, 3M™ Medical Non-woven Tape (Catalogue No. 1776) or 3M™ Elastic Medical Tape (Catalogue No. 9907W) (both from 3M Medical Specialties, USA). To this material at least one radiation absorbing layer 701 may be attached, for example by use of an adhesive or by sewing.

Finally, additional layers and/or material (not shown) may be included in a planar member 710 and/or attached thereto. Non-limiting examples include electrical wiring and/or one or more additional batteries and/or battery components and/or electrical and/or mechanical connectors that may be attached directly or indirectly to planar member 710 (for example such as shown for wire 148 in FIG. 1) and/or embedded in one or more layers and/or between two or more layers of the planar member 710. In some embodiments, planar member 710 may comprise an adhesive coated portion or layer and a removable liner also at its top surface (being remote from the skin), positioned to serve as a connector for attaching one or more additional components (e.g. an EM probe and/or a connector or and/or a cover and/or a battery) to planar member 710. Additional layers may be applied also above battery 720, as long as the electrical connector is accessible for attachment to an EM probe when attached to the planar member 710.

In some embodiments, planar member 710 or one or more layers thereof, further comprises components that may impart rigidity to at least part of the planar member. In some embodiments planar member 710 is constructed such that it is more rigid and/or less flexible in regions that are closer to connector(s) 721 and/or 722 than it is in regions that are closer, for example to a periphery of the planar member 710.

In some embodiments, an adhesive patch is configured to be attached to a user's body for a period of time exceeding 24 hours, or even exceeding a week or two weeks or three weeks or four weeks or 30 days or more. To that end, materials used to construct planar member 700, 710 may be selected to be bio compatible and/or to allow perspiration to be emitted via the planar member, for example as is known in the art for the manufacture of adhesive medical tape or bandages. In some embodiments, one or more layers are perforated. In some embodiments adhesive layer 703, 713 is selected and/or the planar member comprises a coating and/or moisture protecting layer (not shown) so that the adhesive patch will remain attached to a skin of a user despite wetting of its outer surface (e.g. when taking a shower).

In some cases it may be useful to have adhesive patches that would allow the consecutive attachment of one or more EM probes in sequence at the same location on the skin of a user. In this context, two EM probes may be considered to be attached at the same location, at any instance where there is at least some overlap between the contact areas of the two (or more) adhesive patches' bottoms and the skin on the user. In some cases, the degree of overlap is such that will allow an EM probe attached to one probe to transmit and/or sense EM radiation passing through or reflected by the same skin or intra-body region. In some embodiments, this overlap includes an overlap of at least a portion of the openings in the radiation absorbing material layers of the two (or more) adhesive patches. In some embodiments, for example where the adhesive patch does not include an opening (for example if the planar member does not comprise radiation absorbing material), the overlap includes at least a portion of the planar member that is to be positioned under the EM probe, when attached to the planar member.

Attachment of an adhesive patch at the same or a similar location as a previous probe may be performed in many different ways. For example, the location may be measured with respect to the user's body (e.g. a given distance and angle from a prominent body feature, such as, for example a central axis along the spine or sternum of the user, and/or the tip of the upper end of the manubrium of the user). This can be performed for example using a measuring aide (e.g.

a flexible or rigid ruler or measuring tape). Optionally, the measuring aide is attachable to the patch or associated therewith or even marked upon the patch or any portion thereof.

Optionally, placement is performed based on a marking on the user (e.g. on the user's skin or on a garment worn by the user). The marking may be permanent (e.g. a tattoo) or washable (e.g. biodegradable ink). The marking may be applied by the user or a practitioner or may be a result of the placement of the previous patch. For example, the patch may comprise one or more ink stains that would leave a mark on the user's skin when the patch is removed. A second patch may then be alighted at the same location, with a desired degree of overlap, in accordance with the markings left by one or more previous patches. Optionally, the patch is placed atop a marked or dedicated region or opening of a garment worn by the user.

In some embodiments, the adhesive layered at the bottom surface of an adhesive patch may be any adhesive known in the art for attachment of an adhesive patch to the skin of a user. It may be a biocompatible substance and have sufficient adhesion to skin to allow attachment of the patch and EM probe without dislocation for a period of use, but at the same time, be sufficiently loose to allow painless (or low pain) removal of the adhesive patch after use.

In some uses, a first adhesive patch may be attached to a user's skin for attaching an EM probe at the site of attachment, for sensing EM properties of a given body location. At a later time, the first adhesive patch is removed and a second adhesive patch is attached at essentially the same skin area for attaching the same (or a different) EM probe to continue sensing EM properties of the same body location.

In some embodiments, the at least one layer of an adhesive that is attached over at least part of a surface of the planar member is applied to form a pattern comprising at least one adhesive covered portion and at least one adhesive-free portion. The pattern in some embodiments is such that will allow the sequential attachment of a plurality of adhesive patches at overlapping positions with less than 100% overlap between the adhesive-covered portions of the respective patterns at the respective positions.

According to some embodiments, adhesive patches are provided having an adhesive layer having a pattern with at least one adhesive covered portion covering 70% or less of the patch contact surface. As used herein, the patch contact surface is the patch bottom surface, namely the surface of the planar member that is to be facing a user's skin or in contact therewith when in use. In some embodiments, the patch contact surface is a portion of the bottom surface that comes to contact with a user's skin when in use. This contact surface may include or exclude the portion of the patch bottom surface under an opening in the radiation absorbing material layer. In some embodiments, the adhesive pattern comprises at least one adhesive covered portion covering 50% or less of the adhesive patch's contact surface. In some embodiments, the adhesive pattern comprises at least one adhesive covered portion covering at least 10% or at least 25% or even at least 30% or at least 40% of the contact surface.

In cases where the at least one adhesive covered portion forms a pattern of the adhesive layer covers only a portion of the bottom surface of an adhesive patch, at least one other portion of the surface may be left adhesive-free, for example to allow some ventilation (possibly in conjunction with perforation in the adhesive patch). In some embodiments, a skin soothing agent (for example a therapeutic substance, lotion, cream and/or gel) may be layered in some or all the adhesive-free portions of the adhesive patch bottom surface.

In some embodiments, the pattern of the adhesive on the bottom surface of an adhesive patch is such that the adhesive patch may be placed in sequence at different positions on a surface area with the opening in the radiation absorbing material of the adhesive patch at the first position covering a portion of the surface area that at least partially overlaps a portion of the surface area that is covered by the opening in the radiation absorbing material of the adhesive patch at the second position (e.g. by at least 30%, at least 40% or even by at least 75% or at least 90%), but the portion of the surface area covered by the at least one adhesive covered portion of the adhesive patch at the first position overlaps the portion of the surface area covered by the at least one adhesive covered portion of the adhesive patch at the second position by less than 30%, or even by less than 10% or not at all.

In some embodiments, the pattern of the adhesive on the bottom surface of an adhesive patch is such that the adhesive patch may be placed in sequence at different positions on a surface area with the portion of the adhesive patch of the planar member being under an EM probe at the first position covering a portion of the surface area that at least partially overlaps a portion of the adhesive patch of the planar member being under the EM probe at the second position (e.g. by at least 30%, at least 40% or even by at least 75% or at least 90%), but the portion of the surface area covered by the at least one adhesive covered portion of the adhesive patch at the first position overlaps the portion of the surface area covered by the at least one adhesive covered portion of the adhesive patch at the second position by less than 30%, or even by less than 10% or not at all.

In some embodiments, the first adhesive patch and the second adhesive patch are attached to the surface area at the same rotational orientation while in other embodiments the first adhesive patch and the second adhesive patch are attached to the surface area at the same rotational orientations. For example see the relative orientations of the adhesive patches shown in FIG. 18C, which differ by 90°. In some embodiments, the orientations differ by any other degree, for example—180°.

Figure 18A:
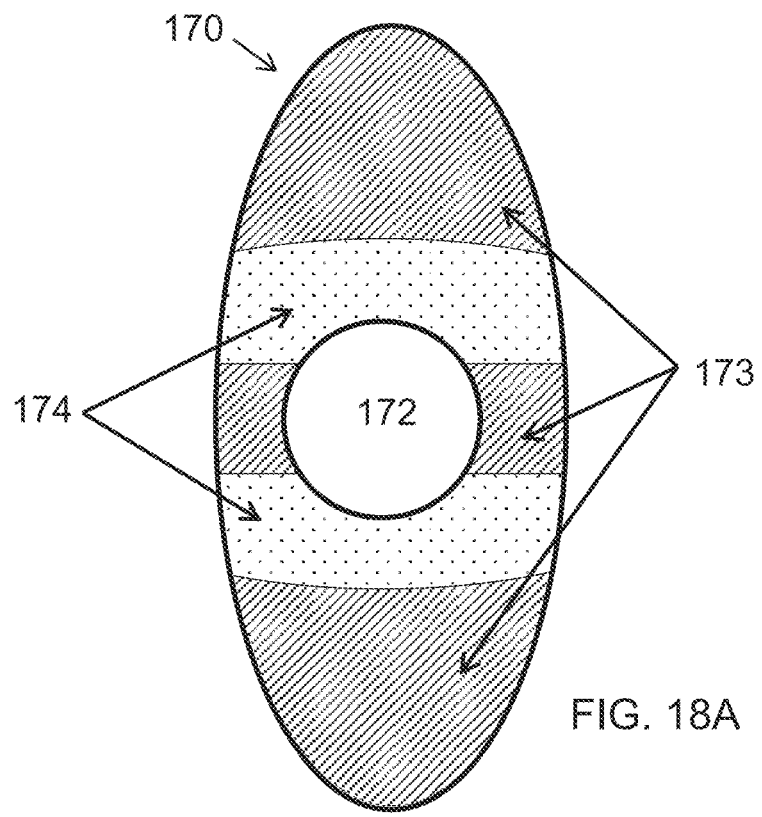
FIGS. 18A to 18C depict a pattern of an adhesive layered on a surface of an adhesive patch, according to some embodiments of the invention.
Figure 18B:
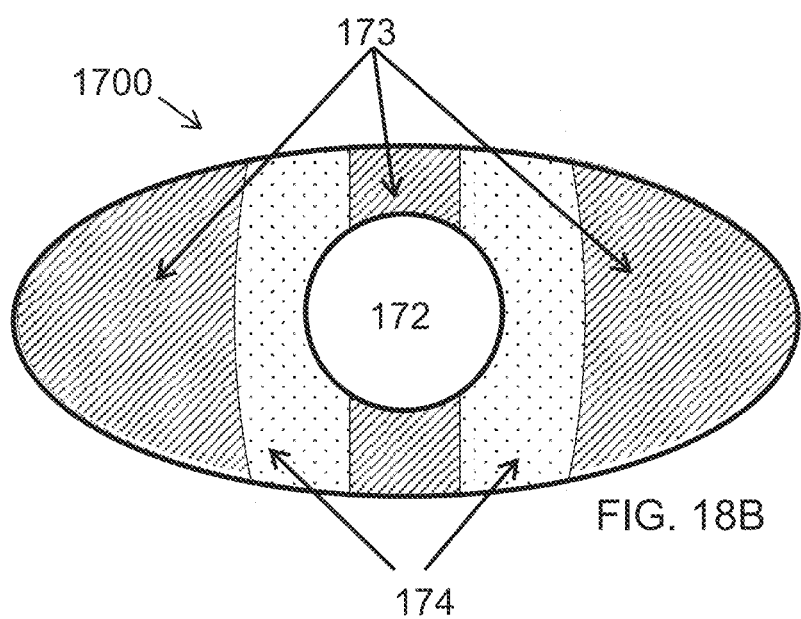
Figure 18C:
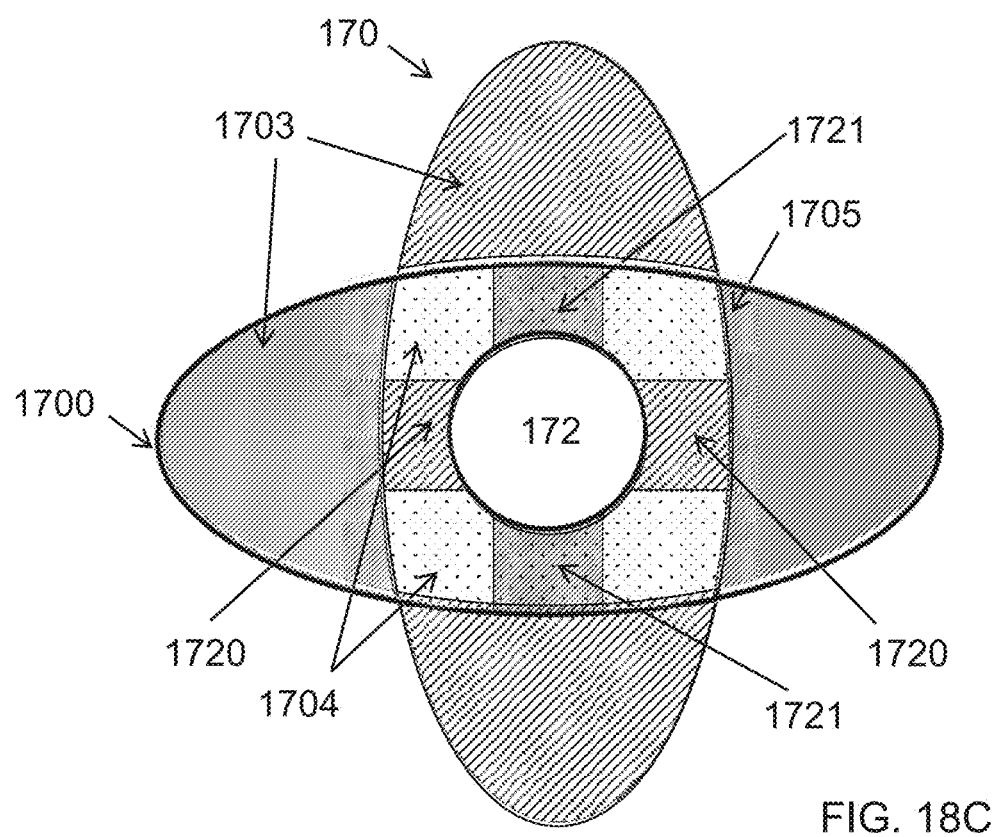

An embodiment of a rotational pattern for an adhesive layer on the bottom of an adhesive patch is depicted schematically in FIGS. 18A-18C. As seen in FIGS. 18A and 18B (showing the adhesive pattern at a first orientation 171 and at a second orientation 1710, being at a 90° angle with respect to the first, when each pattern is positioned on the skin of a user) the bottom surface of the adhesive patch has an opening 172 traversing the patch. Alternatively, the opening 172 does not extend to all layers of the patch. For example, opening 172 may consist of a discontinuity in the adhesive that may be situated at least under a portion of an EM probe when attached to the patch. Some portions of the bottom surface are covered with an adhesive (adhesive-covered portion 173) and some are not (adhesive-free portion 171). Some or all of adhesive-free portions 174 may be left empty and/or include a layer of another substance as mentioned above. FIG. 18C shows a pattern of a first orientation (FIG. 18A) superimposed on that of a second orientation (FIG. 18B). In use, this such an adhesive patch may be used to position opening 172 (and an EM probe associated therewith) at a given location on a user's skin, at first at a first and later, after removal, at a second orientation rotated by 90° at different times.

In some embodiments of the invention the connectors are configured such that they allow the attachment of the EM probe in a plurality or orientations. In some embodiments, this allows attaching a plurality of adhesive patches to a surface at a plurality of orientations one relative to the other (e.g. in sequence) while the EM probe(s) attached to each of the adhesive patches may all have the same orientation.

In the presented overlay of FIG. 18C, while the openings at both orientations are overlapping at about 100% of their surfaces, the adhesive-covered portions 173 of the adhesive patch at the first orientation 171 do not overlap the adhesive-covered portions 173 of the adhesive patch at the second orientation 1710. In regions 1703 adhesive-covered portion 173 of one orientation do not overlap any portions of the other orientation, regardless whether they are adhesive-covered or adhesive-free. In regions 1704, 1720 and 1721 the bottom surfaces overlap, but no two overlapping surfaces are covered with an adhesive. In regions 1704 both patterns have adhesive free portions, while in regions 1720 there is an adhesive-covered portion only in orientation 171 and in regions 1721 there is an adhesive-covered portion only in orientation 1710.

In some embodiments, the adhesive pattern(s) are such that may be overlaid at an offset (with or without rotation), for example with only 75%-99% overlap between the areas covered by two or more adhesive patches (due at least partially to the offset), but the patterns do not overlap by more than 10% or not by more than 20% of the adhesive-covered portions. For example—an adhesive pattern may comprise a plurality of dots or narrow longitudinal and/or vertical lines (e.g. 3 mm wide or less or even 1 mm wide or less) covering a total of less than 40% or even less than 30% of the total bottom surface of the patch, and having adhesive free gaps between the lines and/or dots being at least 150% wider than the width of the respective adhesive covered dots and/or lines.

In some embodiments a set of adhesive patches is provided comprising adhesive patches having different patterns of adhesive on the their respective bottom surfaces, each pattern comprising at least one adhesive-free portion and at least one adhesive-covered portion. The patterns in some embodiments are selected such a plurality of adhesive patches may be attached in sequence to the same placement area such that a first adhesive patch may be placed with the opening in its radiation absorbing material layer covering a portion of the placement area which at least partially overlaps the portion of the placement area that is covered by the opening in the radiation absorbing material layer of a second adhesive patch (e.g. by at least 30%-40% or even by at least 75%), but the portion of the placement surface that is covered by the at least one adhesive-covered portion of the first adhesive patch overlaps the portion of the placement surface that is covered by the at least one adhesive-covered portion of the second adhesive patch by less than 30% (of the adhesive covered area), or even by less than 10% or not at all. To this end, and subject to the patterns of adhesive, the adhesive patches may be positioned at the same orientation or at different orientations one with respect to the other.

In some embodiments a set of adhesive patches is provided comprising adhesive patches having different patterns of adhesive on the their respective bottom surfaces, each pattern comprising at least one adhesive-free portion and at least one adhesive-covered portion. The patterns in some embodiments are selected such a plurality of adhesive patches may be attached in sequence to the same placement area such that a first adhesive patch may be placed with the portion of the adhesive patch of the planar member being under an EM probe covering a portion of the placement area which at least partially overlaps the portion of the placement area that is covered by a portion of the adhesive patch of the planar member being under an EM probe of a second adhesive patch (e.g. by at least 30%-40% or even by at least 75%), but the portion of the placement surface that is covered by the at least one adhesive-covered portion of the first adhesive patch overlaps the portion of the placement surface that is covered by the at least one adhesive-covered portion of the second adhesive patch by less than 30% (of the adhesive covered area), or even by less than 10% or not at all. To this end, and subject to the patterns of adhesive, the adhesive patches may be positioned at the same orientation or at different orientations one with respect to the other.

In some embodiments a set of adhesive patches is provided comprising adhesive patches having such patterns of adhesive on the bottom surfaces of the adhesive patches such that a first adhesive patch and a second adhesive patch may be placed in sequence over the same placement surface such that the portion of the placement surface that is covered by the bottom surface of the first adhesive patch overlaps the portion of the placement surface that is covered by the surface of the second adhesive patch by at least 50% or even by at least 90% or even 100% overlap, and the portion of the placement surface that is covered by the at least one adhesive-covered portion of the first adhesive patch overlaps the portion of the placement surface that is covered by the at least one adhesive-covered portion of the second adhesive patch by less than 30%, or even not at all. To this end, and subject to the patterns of adhesive, the adhesive patches may be positioned at the same orientation or at different orientations one with respect to the other.

Figure 19A:
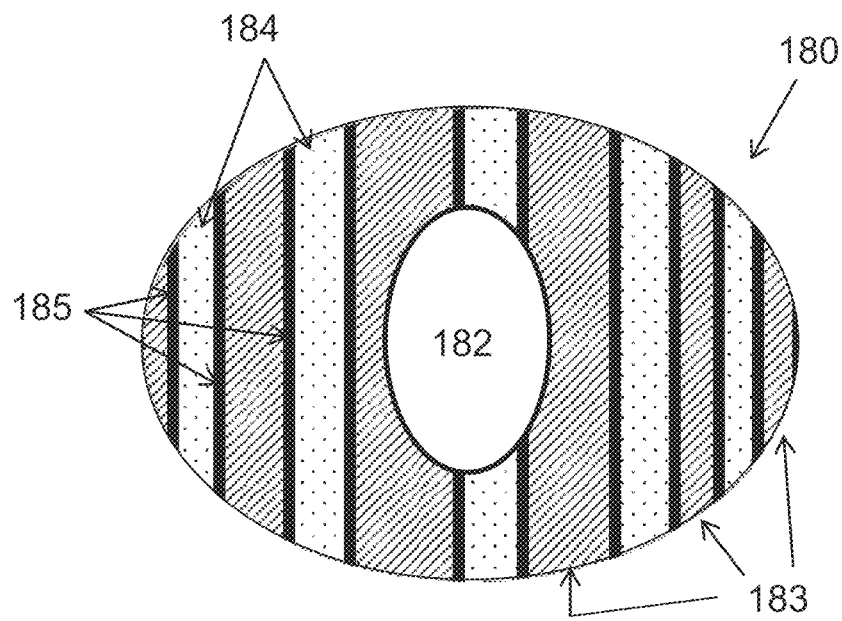
FIGS. 19A and 19B depict two alternative patterns of an adhesive layered on a surface of an adhesive patch, according to some embodiments of the invention.
Figure 19B:
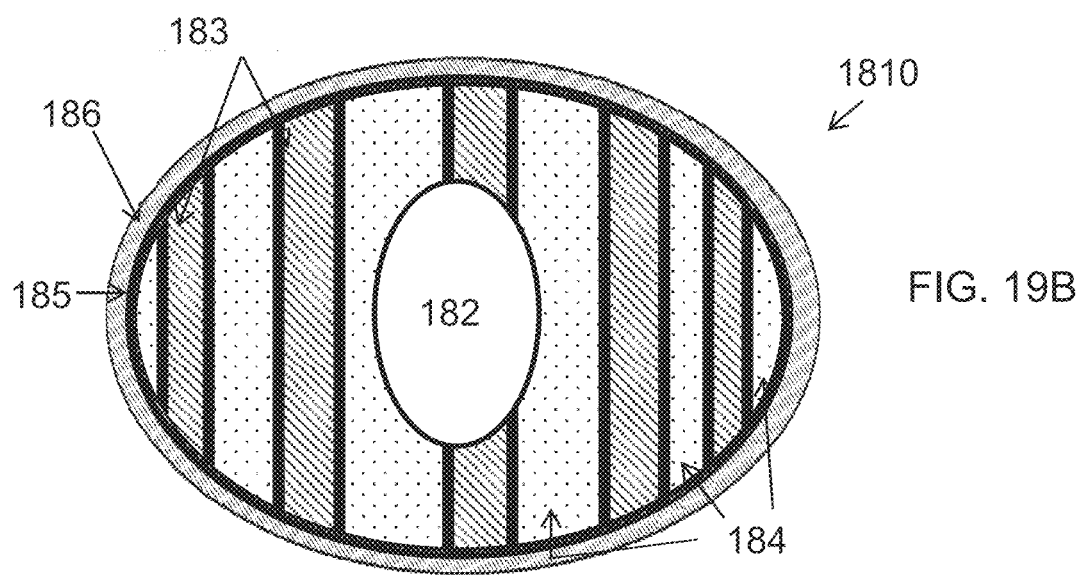
Figure 19C:
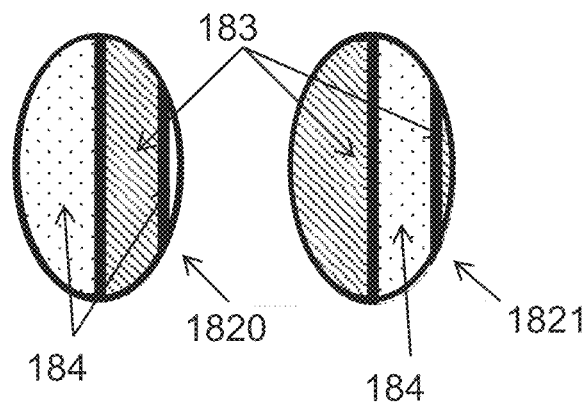
FIG. 19C depicts depict two alternative patterns of an adhesive layered on a portion thereof of an adhesive patch, according to some embodiments of the invention.

Attention is now drawn to an example of a set of patches depicted in FIGS. 19A-19C. In this example, the adhesive patterns on the bottoms of a first adhesive patch 181 and a second adhesive patch 1810 are shown, each having adhesive-covered portions 183, adhesive-free portions 184 and an opening 182 in the layer of radiation absorbing material in the adhesive patch. As seen, the adhesive-covered portions 183 and adhesive-free portions 184 in both adhesive patches are in the form of vertical bars, but in different arrangements: where there is an adhesive-covered portion 183 in the first adhesive patch pattern 181, there is a non-adhesive-covered portion 184 in the second adhesive patch pattern 1810, and vice versa. Therefore, the patches may be overlaid at the exact same position, with the adhesive-covered portions of one not overlapping those of the other. At times, the precise position and size of the adhesive-covered portions 143 may vary such that some overlap between adhesive-covered portions of the first patch over adhesive-covered portions of the second patch is allows (e.g. less than 30%).

In use, a user may position the patches at the same position with imperfect precision, which may cause or increase overlap between adhesive-covered portions of the patches. In order to reduce the chances of such unintentional overlap a patch pattern of two or more patches in a set may be selected to include portions that are free of adhesive in both patterns. This is schematically depicted as thick lines 185 in FIGS. 19A and 19B.

Optionally, a plurality of adhesive patches in a set have the same size and shape. Optionally, some adhesive patches in a set might have different sizes and/or different shapes. This is depicted for example schematically by a circumferential ring 186 in FIG. 19B. This ring may be, for example, sized to be outside the outer boundary of the pattern of adhesive patch 180 when superimposed over adhesive patch pattern 1810. Thus, circumferential ring 186 may be covered partially or completely with adhesive, as it may not overlap any adhesive-covered portion 183 of adhesive patch pattern 181.

Optionally, an adhesive pattern may be placed under opening 182. An example for patterns of adhesive under an opening in a patch is depicted in FIG. 19C. In this example, each of pattern 1820 and pattern 182 has adhesive-covered portion(s) 183, but at different positions, such that the patterns may be superimposed one on the other and the adhesive-covered portions will not overlap or only slightly overlap (with less than 30% overlap).

In some embodiments (for example as depicted in FIG. 19B) the adhesive pattern under the opening is provided separately from the adhesive pattern of the patch. For example, the EM probe may be attached to an adhesive pattern at its bottom and later both are connected to an adhesive patch according to any of the above embodiments.

Figure 20A:
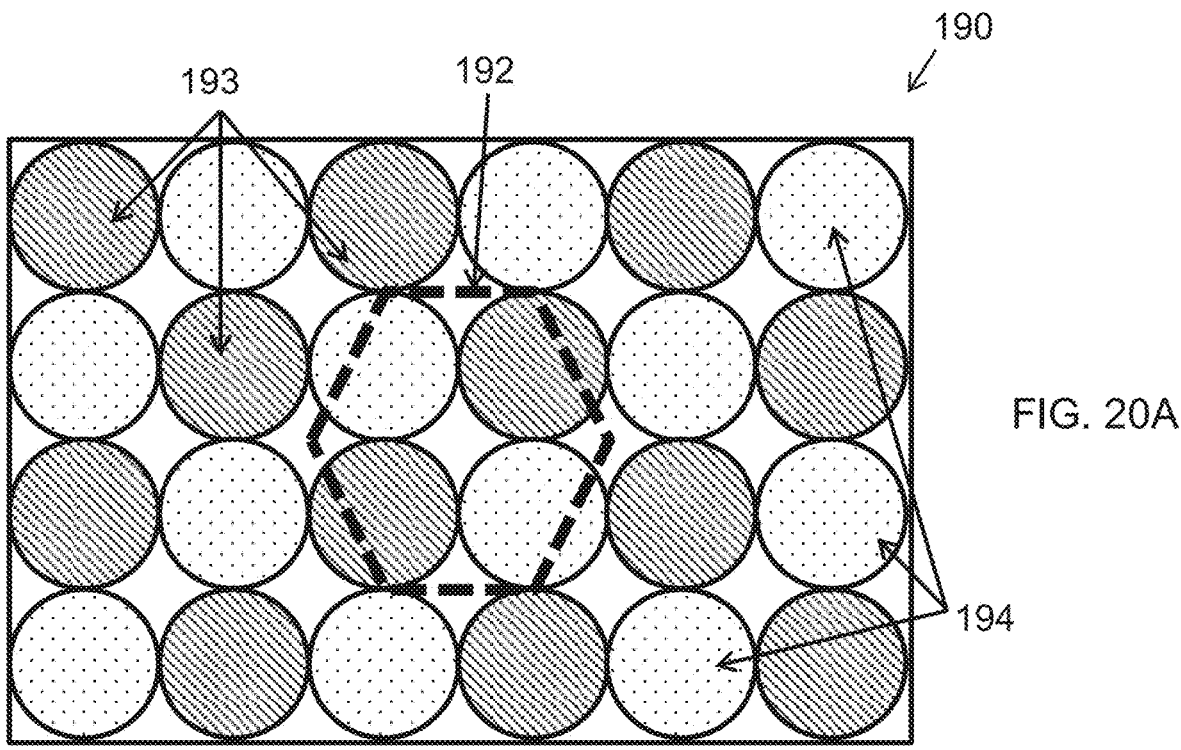
FIGS. 20A and 20B depict two alternative patterns of an adhesive layered on a surface of an adhesive patch, according to some embodiments of the invention.
Figure 20B:
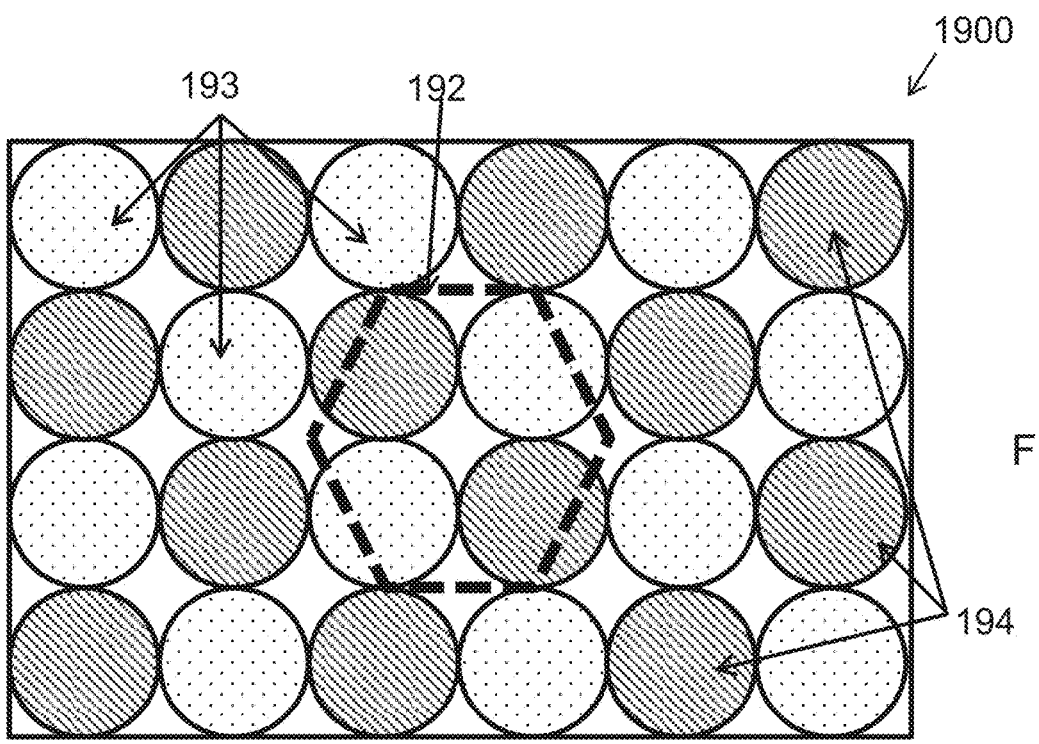

In some embodiments, the adhesive patch may be provided with an adhesive pattern extending both under the radiation absorbing material layer and the opening (or where there is no opening). A set of adhesive patches having one example for such a pattern is shown in FIGS. 20A and 20B. In this example, the adhesive patterns 190 and 1900 (and optionally also the planar members of the corresponding adhesive patches) have an essentially rectangular shape. The location of an opening 192 is depicted by a dashed line. In this example, adhesive patterns 190 and 1900 comprise circular adhesive-covered portions 193 and circular non-adhesive-covered portions 194.

In some embodiments, the adhesive covered portion of one adhesive patch is larger than the adhesive covered portion of another adhesive patch, thereby covering a greater portion of the placement surface. In some such embodiments, the percentage of overlap is calculated as a percentage of the portion of the placement surface that is covered by the adhesive covered portion having a larger area. In other such embodiments, the above percentage of overlap is calculated as a percentage of the portion of the placement surface that is covered by the adhesive covered portion having a smaller area.

EXAMPLES

Reference is now made to the following examples, which together with the above descriptions, illustrate some embodiments of the invention in a non-limiting fashion.

Figure 11A:
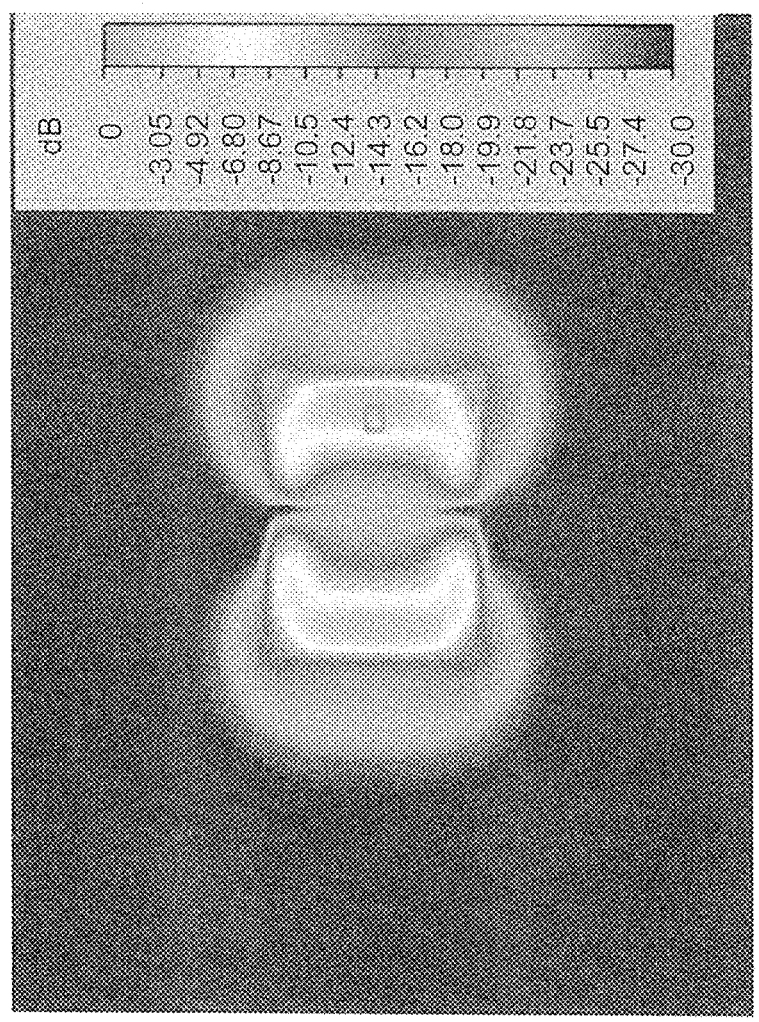
FIGS. 11A, 11B and 11C are images of surface current density in an EM probe without a layer of absorbing material, in an EM probe with a layer of absorbing material, and in an EM probe with a layer of absorbing material covering the bottom side only of a circumferential flange, according to some embodiments of the present invention.
Figure 11B:
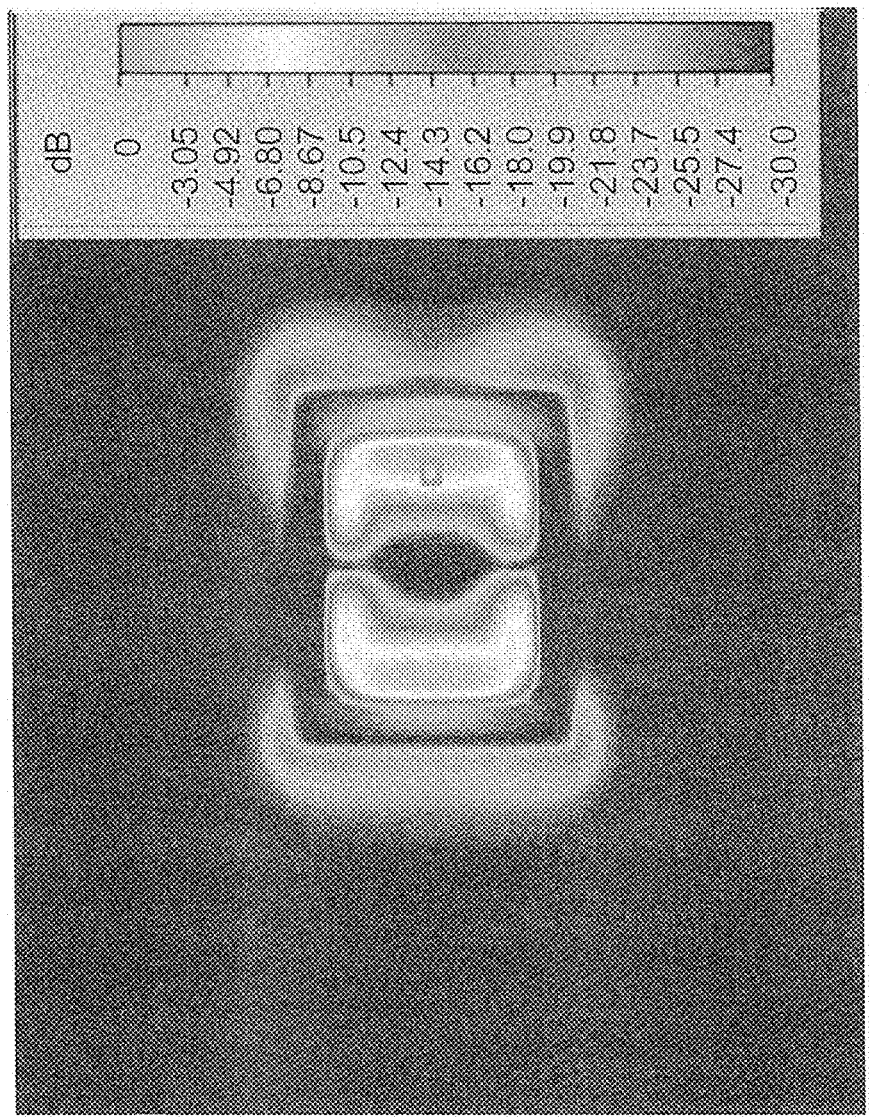
Figure 11C:
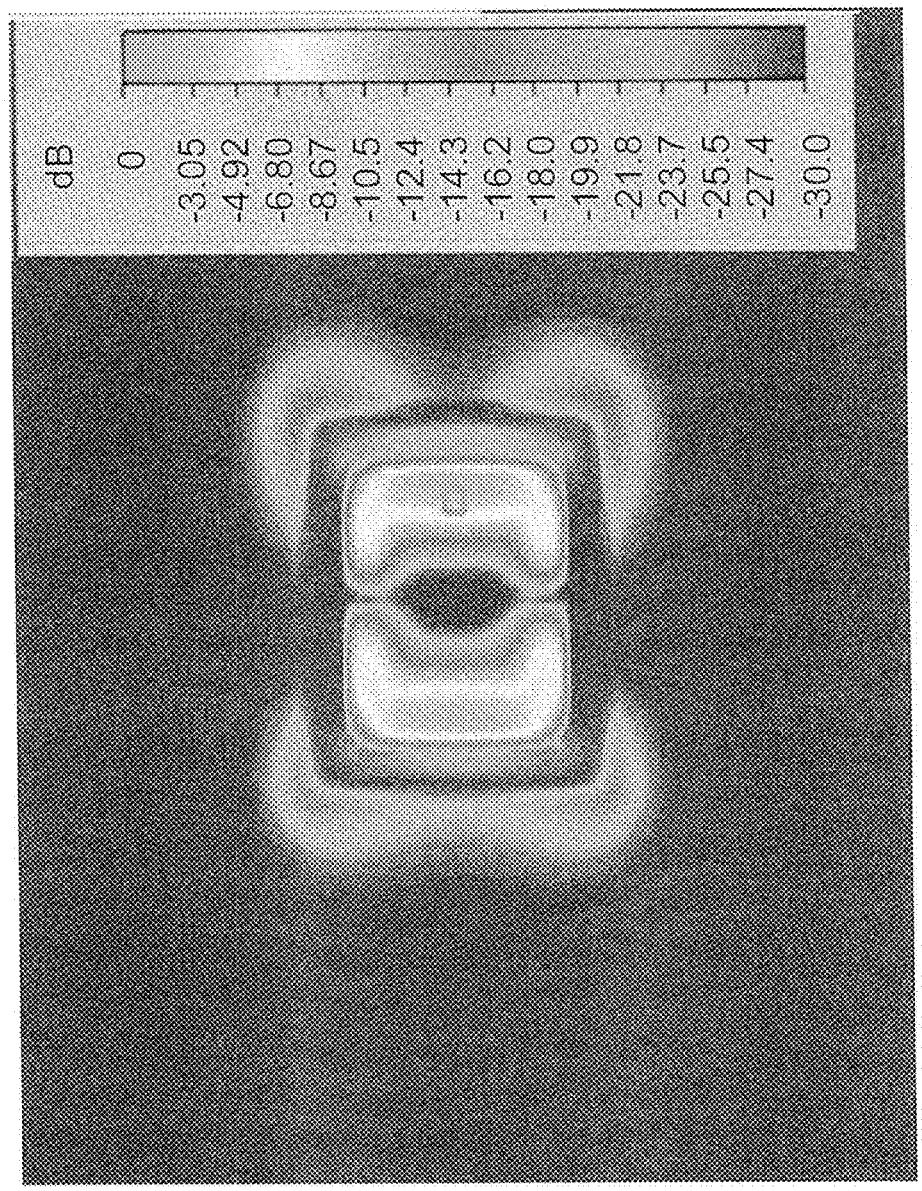
Figure 12A:
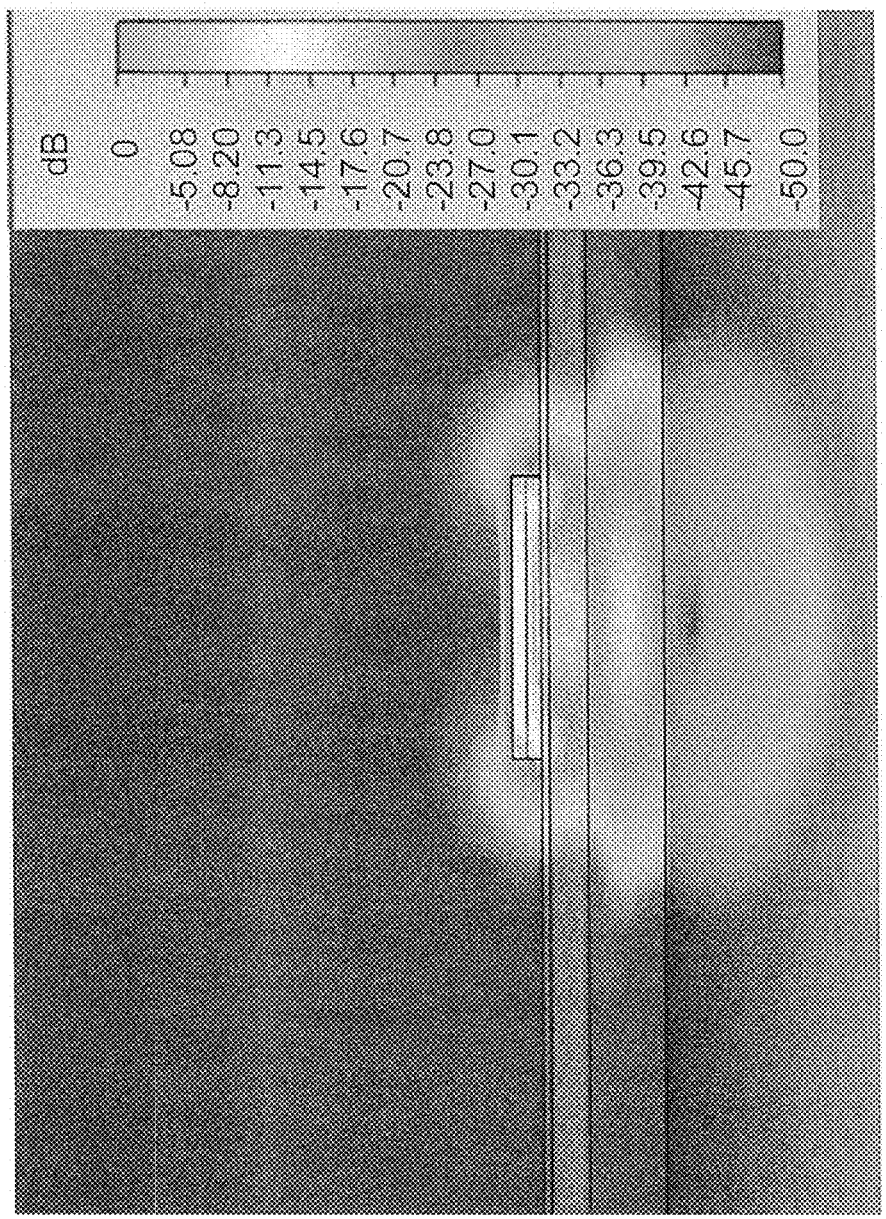
FIGS. 12A and 12B and 12C are images of H-field distribution in an EM probe without a layer of absorbing material, in an EM probe with a layer of absorbing material, and in an EM probe with a layer of absorbing material covering the bottom side only of a circumferential flange, according to some embodiments of the present invention.
Figure 12B:
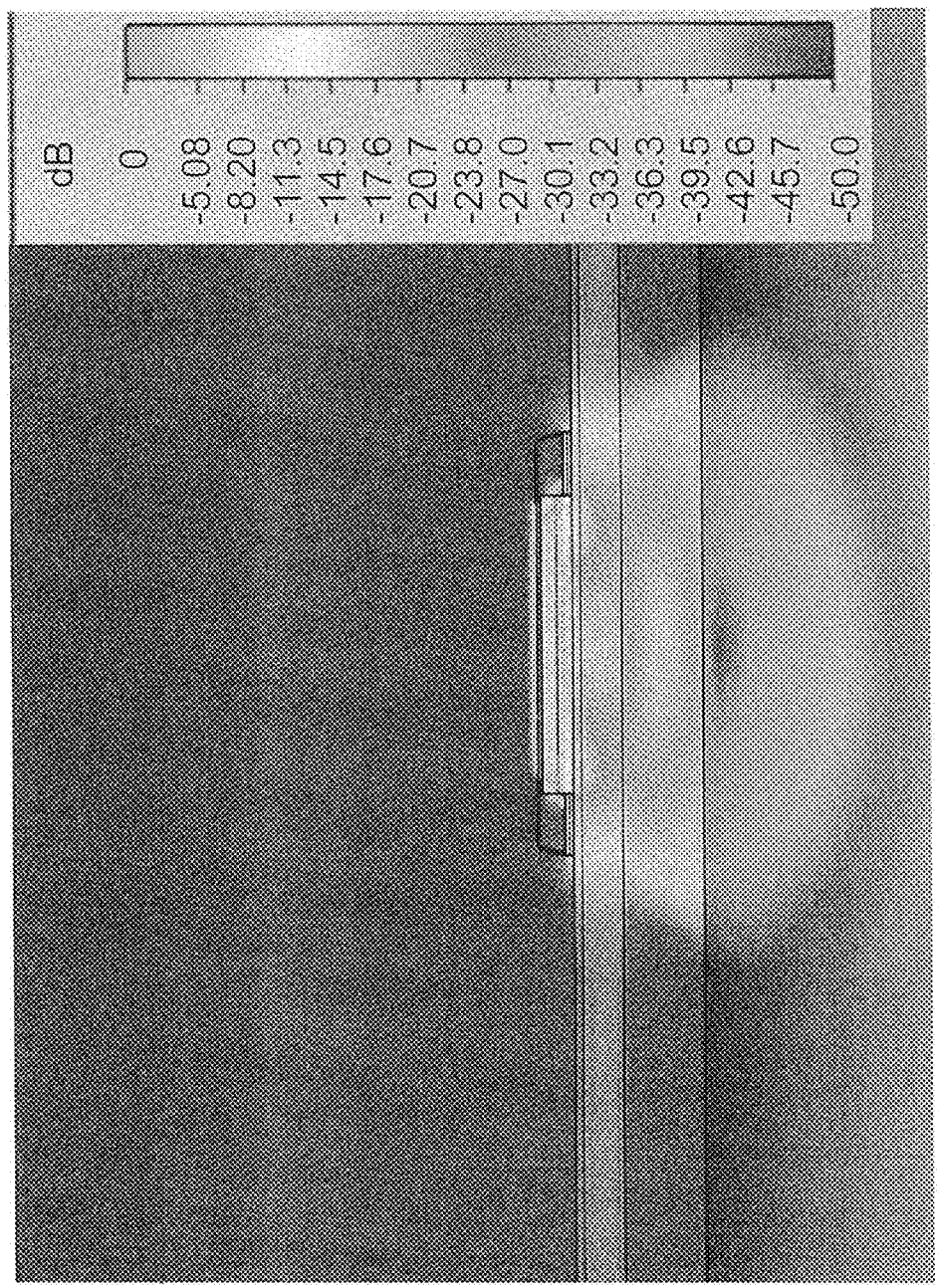
Figure 12C:
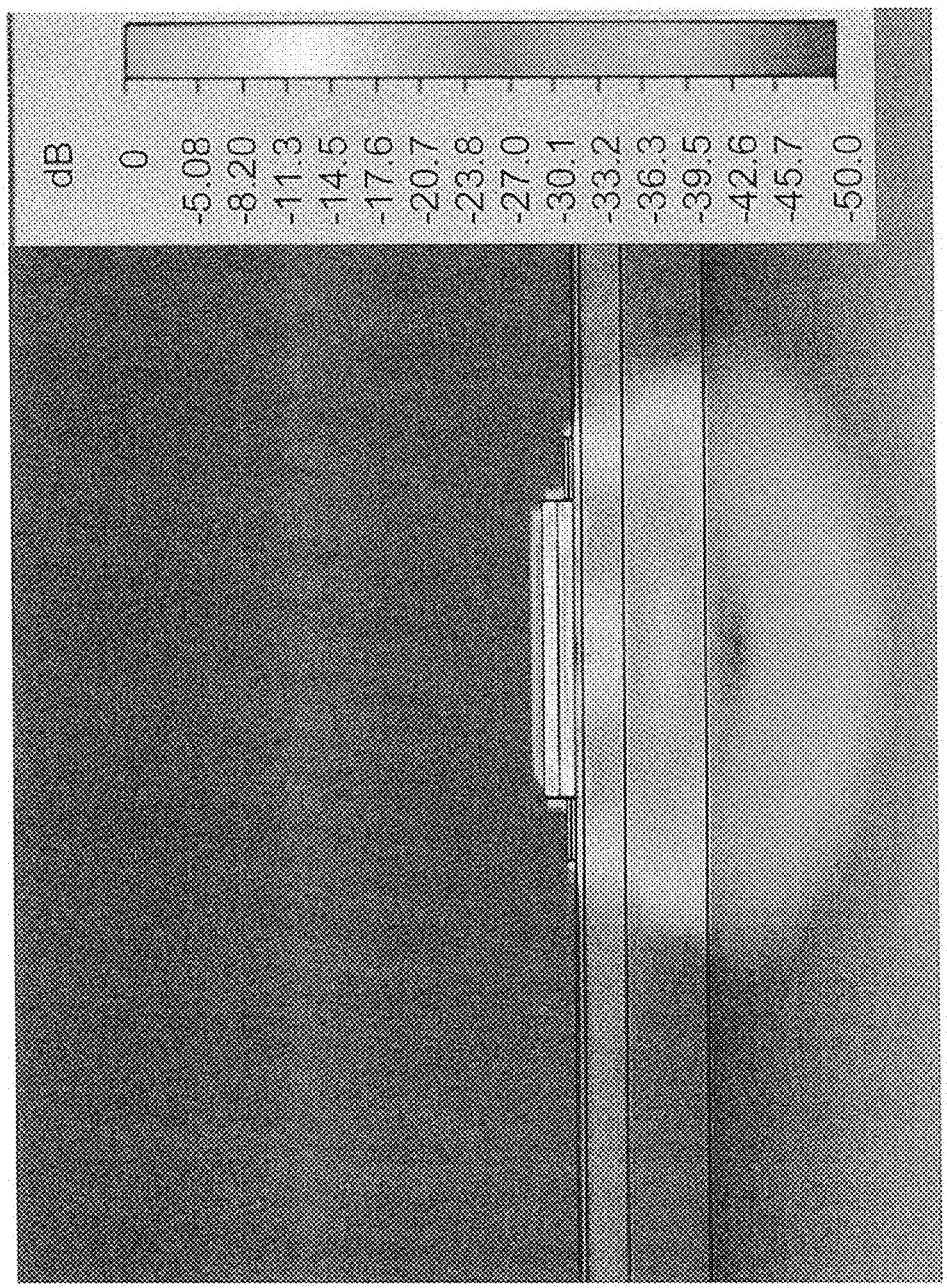
Figure 13A:
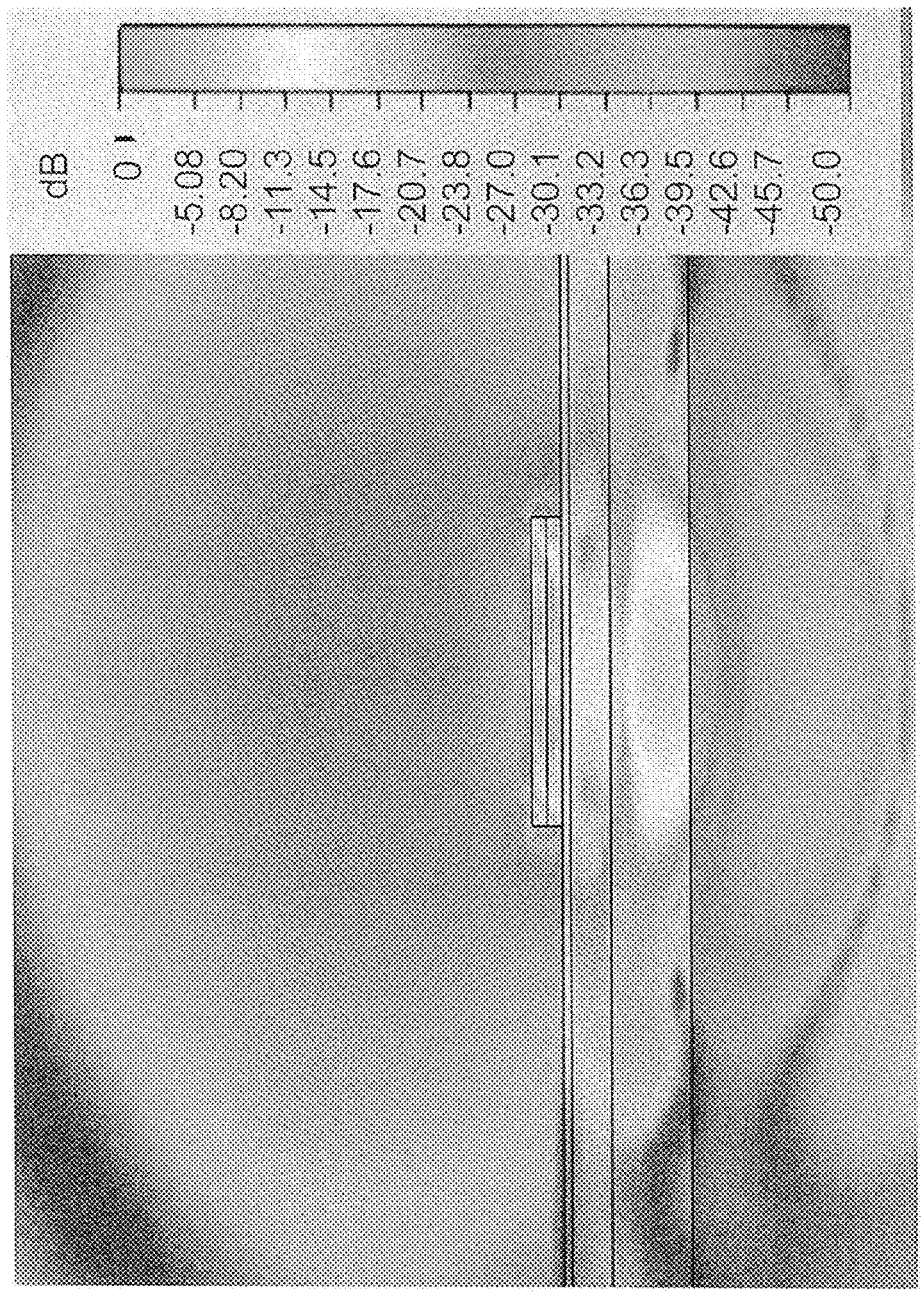
FIGS. 13A and 13B and 13C are images of E-field distribution in an EM probe without a layer of absorbing material, in an EM probe with a layer of absorbing material, and in an EM probe with a layer of absorbing material covering the bottom side only of a circumferential flange, according to some embodiments of the present invention.
Figure 13B:
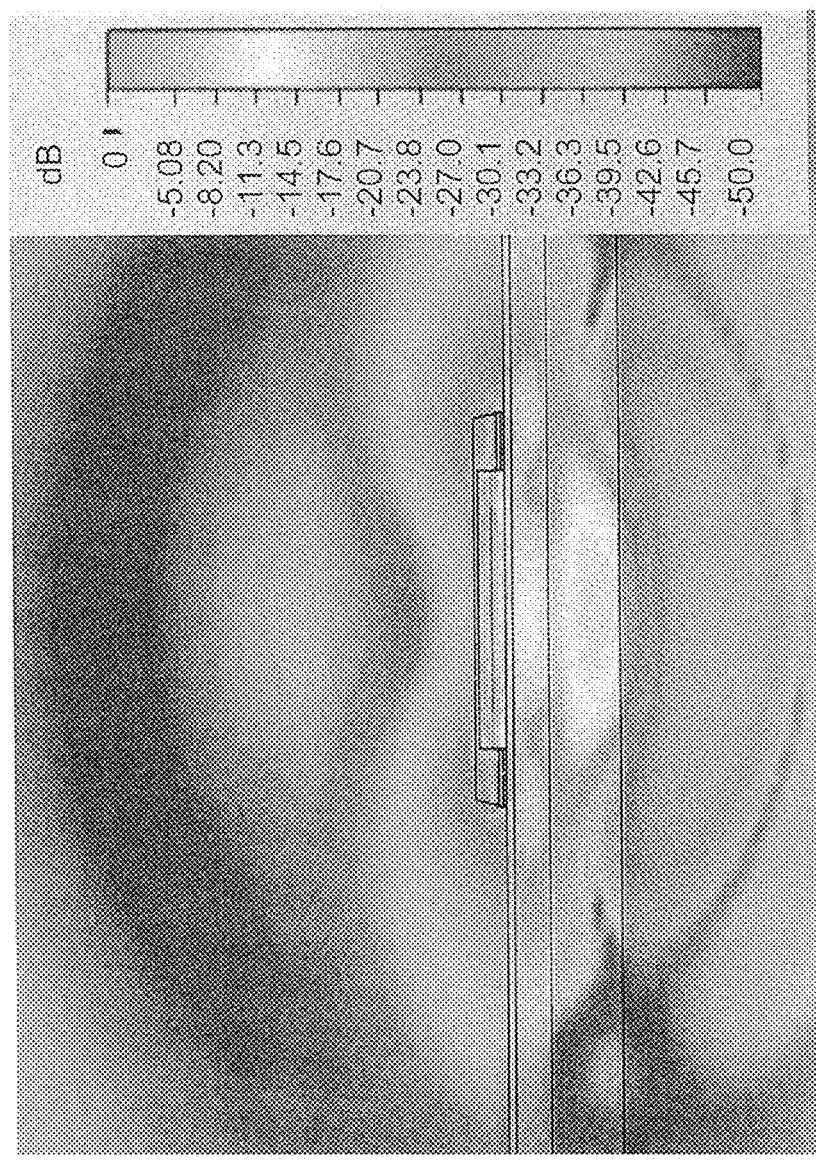
Figure 13C:
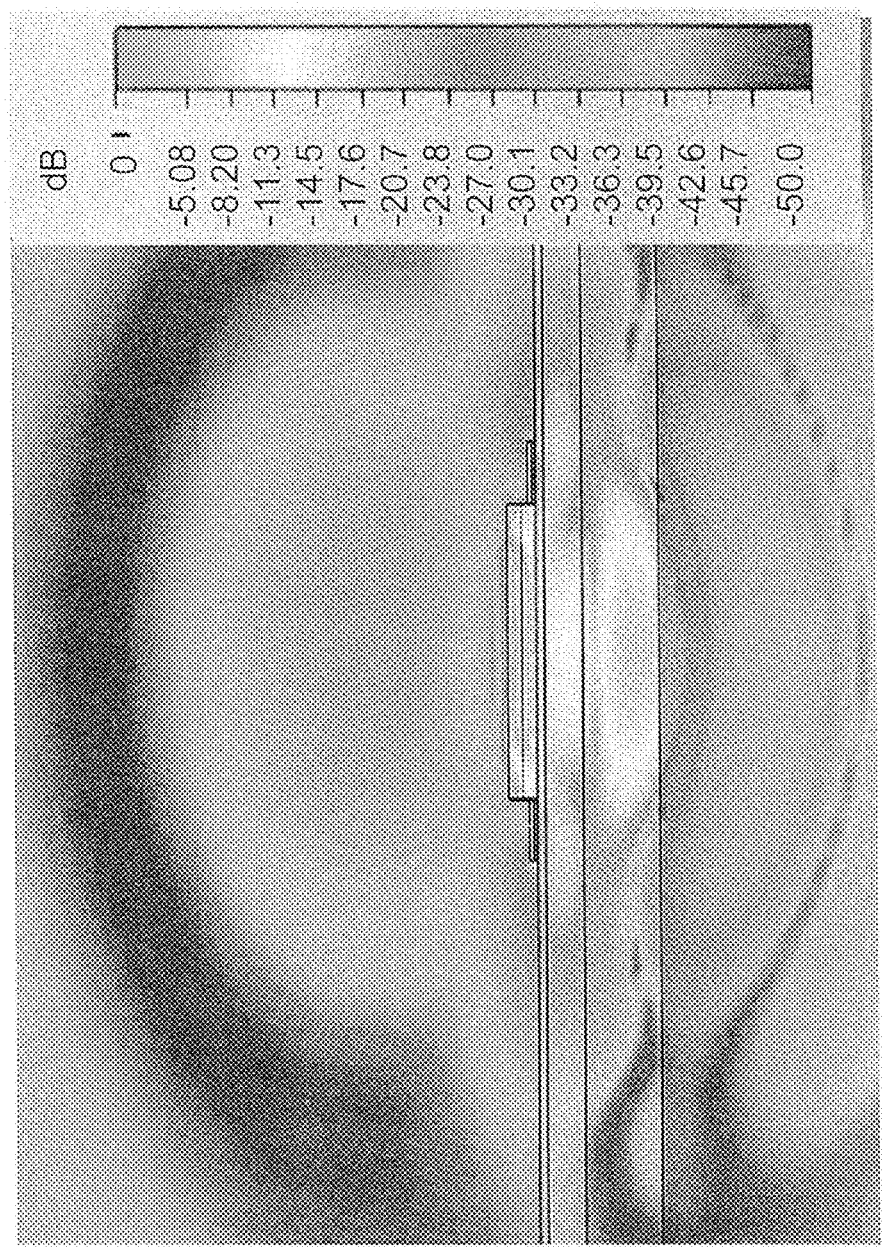

Reference is now made to FIGS. 11A, 11B and 11C, which are images of respectively, surface current density in an EM probe without a layer of absorbing material and a surface current density in an EM probe with a layer of absorbing material covering both sides of a circumferential flange as well as covering a cup shaped cavity, and a current density in an EM probe with a layer of absorbing material covering the bottom side only of a circumferential flange, according to some embodiments of the present invention. Reference is also made to FIGS. 12A, 12B and 12C, which are images of, respectively, H-field distribution in an EM probe without a layer of absorbing material and a H-field distribution in an EM probe with a layer of absorbing material covering both sides of a circumferential flange as well as covering a cup shaped cavity, and an H-field distribution in an EM probe with a layer of absorbing material covering the bottom side only of a circumferential flange, according to some embodiments of the present invention. Reference is also made to FIGS. 13A, 13B and 13C, which are images of, respectively, E-field distribution in an EM probe without a layer of absorbing material, E-field distribution in an EM probe with a layer of absorbing material covering both sides of a circumferential flange as well as covering a cup shaped cavity, and an E-field distribution in an EM probe with a layer of absorbing material covering the bottom side only of a circumferential flange, according to some embodiments of the present invention. FIGS. 11-13 depict a simulation of an EM probe having an antenna mounted in an inner volume of a cup shape cavity. The antenna radiates RF radiation in a frequency belonging to band of about 0.4 Ghz or 0.9 Ghz or 2.4 Ghz or 5.6 Ghz or belonging to a UWB band, for example in 3-6 Ghz band, or another frequency or band in the UHF band. The sizes of the cup shape cavity is optionally of a square shape of dimension about 2, 4, 5, 7, 10, 13, 17 or 20 centimeters and the antenna is sized to spanning 20, 30, 50, 80, 90, or 95% of the width of the cavity. As depicted by these figures, the layer of absorbing material isolates the radiated area and limits it to the inner volume of the EM probe.

It is expected that during the life of a patent maturing from this application many relevant devices and methods will be developed and the scope of the term transducer, cavity, absorbing material, and controller is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible EM radiation absorbing substrate-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for propagating radiofrequency (RF) radiation towards a subject's body, the apparatus comprising:
    an electromagnetic (EM) probe having a cup-shaped cavity made of a conductive material, the cup-shaped cavity having an opening and an interior volume, and at least one antenna adapted to radiate RF radiation towards the subject's body, the at least one antenna is located:
    (a) in said interior volume, or
    (b) outside of said interior volume and connected by at least one waveguide or at least one cable to said cup shaped cavity;
    an adhesive patch comprising a planar member formed around said cup-shaped cavity, in proximity to said opening, and comprising at least one layer of RF radiation absorbing material, the at least one layer of RF radiation absorbing material defining at least one opening formed therein, the at least one opening configured to allow the propagation of RF radiation therethrough, and at least one layer of an adhesive at least partially attached over a bottom surface of the planar member,
    wherein the at least one layer of adhesive extends at least partially below at least one of the at least one opening, and the at least one layer of adhesive is formed of a material that attenuates EM energy by not more than 20 dB; and
    wherein said at least one antenna is adapted to emit RF radiation towards the subject's body via said interior volume and via the at least one opening configured to allow the propagation of RF radiation originated from the at least one antenna via the at least one opening from one side of the planar member to the other;
    wherein said RF radiation absorbing material is selected from the group of materials having at least one of the following:
    a permeability loss tangent of $(\tan \delta = \mu''/\mu') > 0.01$ for all RF radiation frequencies within the range of 100 MHz-5 GHz;
    a permittivity loss tangent of $(\tan = E''/E) > 0.01$ for all RF radiation frequencies within the range of 100 MHz-5 GHz; and
    a partial conduciveness manifested by a surface resistivity between 20 and 10,000 Ohm per square (Q/sq);
    wherein said RF radiation absorbing material comprises a volumetric resistivity greater than $10^{-3}$ Ohm meter (Qm).

2. The apparatus of claim 1, comprising a battery for providing power to the EM probe when the EM probe is attached to the adhesive patch.

3. The apparatus of claim 1, comprising a cover positioned over the opening, the cover being shaped and sized to receive the antenna.

4. The apparatus of claim 1, wherein the at least one layer of adhesive extends below at least one of the at least one opening.

5. The apparatus of claim 1, wherein said adhesive is attached to the bottom surface at a pattern comprising at least one adhesive-covered portion and at least one adhesive-free portion, wherein the pattern is such that the adhesive patch is attached to a surface area at at least a first position and at a second position such that:
    the portion of the surface area that is covered by the at least one opening of the adhesive patch at the first position overlaps the portion of the surface area covered by the opening of the adhesive patch at the second position by at least 30%; and
    the portion of the surface area that is covered by the at least one adhesive-covered portion of the adhesive patch at the first position overlaps the portion of the surface area that is covered by the at least one adhesive-covered portion of the adhesive patch at the second position by less than 30%.

6. The apparatus of claim 5, wherein the portion of the surface area covered by the adhesive patch at the first position overlaps the portion of the surface area covered by the adhesive patch at the second position by at least 90%.

7. The apparatus of claim 5, wherein the patch at the first position is at a first rotational orientation and the patch at the second position is at a second rotational orientation being different from the first rotational orientation.

8. The apparatus of claim 7, wherein the first rotation differs from the second rotation by about 180°.

9. The apparatus of claim 7, wherein the first rotation differs from the second rotation by about 90°.

10. The apparatus of claim 5, wherein the portion of the surface area that is covered by the at least one adhesive-covered portion of the adhesive patch at the first position overlaps the portion of the surface area that is covered by the at least one adhesive-covered portion of the adhesive patch at the second position by less than 10%.

11. The apparatus of claim 10, wherein the portion of the surface area that is covered by the at least one adhesive-covered portion of the adhesive patch at the first position does not overlap the portion of the surface area that is covered by the at least one adhesive-covered portion of the adhesive patch at the second position.

12. The apparatus of claim 5, wherein the pattern comprises at least one adhesive-covered portion positioned under at least one of the at least one opening.

13. The apparatus of claim 1, further comprising a set of adhesive patches according to claim 1, the set comprising:
   a first adhesive patch having an adhesive attached over at least part of its surface at a first pattern, the first pattern comprising at least one adhesive-covered portion and at least one adhesive-free portion; and
   a second adhesive patch having an adhesive attached over at least part of its surface at a second pattern, the second pattern comprising at least one adhesive-covered portion and at least one adhesive-free portion;
   wherein the first pattern and the second pattern are such that the first adhesive patch and the second adhesive patch are attached to a placement area with the portion of the placement area that is covered by the first adhesive patch overlapping the portion of the placement area that is covered by the second adhesive patch by at least 50%, and the portion of the placement area that is covered by the at least one adhesive-covered portion of the first adhesive patch overlaps the portion of the placement area that is covered by the at least one adhesive-covered portion of the second adhesive patch by less than 30%.

14. The apparatus of claim 1, wherein the adhesive patch further comprises a further adhesive layer arranged at least partially within at least one of the at least one opening and configured to adhere the EM probe thereto.

\* \* \* \* \*